(12) United States Patent
Kapadia

(10) Patent No.: US 10,799,360 B2
(45) Date of Patent: Oct. 13, 2020

(54) SYSTEMS AND METHODS FOR TREATING A REGURGITANT HEART VALVE

(71) Applicant: THE CLEVELAND CLINIC FOUNDATION, Cleveland, OH (US)

(72) Inventor: Samir Kapadia, Chagrin Falls, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 291 days.

(21) Appl. No.: 15/968,000

(22) Filed: May 1, 2018

(65) Prior Publication Data

US 2018/0243087 A1 Aug. 30, 2018

Related U.S. Application Data

(60) Continuation-in-part of application No. 14/883,819, filed on Oct. 15, 2015, now Pat. No. 10,213,304, (Continued)

(51) Int. Cl.
*A61F 2/24* (2006.01)
*A61M 29/02* (2006.01)

(52) U.S. Cl.
CPC ............ *A61F 2/246* (2013.01); *A61F 2/2466* (2013.01); *A61M 29/02* (2013.01); *A61F 2250/001* (2013.01); *A61F 2250/0004* (2013.01)

(58) Field of Classification Search
CPC ...... A61F 2/246; A61F 2/2463; A61F 2/2466; A61F 2/2427; A61F 2/24; A61F 2/2487;
(Continued)

(56) References Cited

U.S. PATENT DOCUMENTS 6,152,144 A   11/2000 Lesh et al.
7,282,023 B2  10/2007 Frering
(Continued)

FOREIGN PATENT DOCUMENTS

WO   2008/141322 A1   11/2008
WO   2009/053952 A2    4/2009

OTHER PUBLICATIONS

PCT International Search Report and Written Opinion for corresponding International Application Serial No. PCT/US2012/048499, dated Jan. 23, 2013, pp. 1-12.

*Primary Examiner* — Melanie R Tyson
(74) *Attorney, Agent, or Firm* — Tarolli, Sundheim, Covell & Tummino LLP

(57) ABSTRACT

A system for treating regurgitation of blood through a diseased heart valve having at least two leaflets can include an implantable, lollipop-shaped device and an adjustment mechanism. The device can have a proximal end portion, a distal end portion, and an intermediate portion extending therebetween. The intermediate portion can include an expandable occluding member having a selectively adjustable diameter and a biocompatible layer attached to at least a portion thereof. The distal end portion can include an anchoring member. The adjustment member can include a distal connecting end that is operatively connected to the proximal end portion of the device. Operation of the adjustment member, after implantation of the device, can cause the diameter of the occluding member to change so that at least one of the heart leaflet coapts with a portion of the occluding member to mitigate or prevent regurgitation of blood through the diseased heart valve.

13 Claims, 19 Drawing Sheets

Related U.S. Application Data which is a division of application No. 13/559,900, filed on Jul. 27, 2012, now Pat. No. 9,161,837.

(60) Provisional application No. 62/492,379, filed on May 1, 2017, provisional application No. 61/512,170, filed on Jul. 27, 2011.

(58) Field of Classification Search
CPC ...... A61F 2/2457; A61F 2/2454; A61F 2/243; A61F 2250/001; A61F 2250/0004; A61M 29/00; A61M 29/02; A61M 2029/025; A61B 2017/00243
See application file for complete search history.

(56) References Cited

U.S. PATENT DOCUMENTS

| | | |
|---|---|---|
| 8,092,525 B2 | 1/2012 | Eliasen et al. |
| 8,216,302 B2 | 7/2012 | Wilson et al. |
| 8,449,606 B2 | 5/2013 | Eliasen et al. |
| 8,480,730 B2 | 7/2013 | Maurer et al. |
| 8,486,136 B2 | 7/2013 | Maurer et al. |
| 8,506,623 B2 | 8/2013 | Wilson et al. |
| 8,517,915 B2 | 8/2013 | Perron et al. |
| 8,523,883 B2 | 9/2013 | Saadat |
| 8,597,347 B2 | 12/2013 | Maurer et al. |
| 8,778,017 B2 | 7/2014 | Eliasen et al. |
| 8,784,480 B2 | 7/2014 | Taylor et al. |
| 9,161,837 B2 * | 10/2015 | Kapadia ................. A61F 2/246 |
| 2002/0042628 A1 | 4/2002 | Chin et al. |
| 2004/0143283 A1 | 7/2004 | McGill et al. |
| 2004/0204738 A1 | 10/2004 | Weber et al. |
| 2004/0243227 A1 | 12/2004 | Starksen et al. |
| 2005/0015109 A1 | 1/2005 | Lichtenstein |
| 2005/0149182 A1 | 7/2005 | Alferness et al. |
| 2005/0222488 A1 | 10/2005 | Chang et al. |
| 2006/0241745 A1 | 10/2006 | Solem |
| 2006/0276890 A1 | 12/2006 | Solem et al. |
| 2007/0021751 A1 | 1/2007 | Reay-Young et al. |
| 2007/0061010 A1 | 3/2007 | Hauser et al. |
| 2007/0066863 A1 | 3/2007 | Rafiee et al. |
| 2007/0093890 A1 | 4/2007 | Eliasen et al. |
| 2007/0203457 A1 * | 8/2007 | Kohn ................. B01L 3/0234 604/187 |
| 2007/0255399 A1 | 11/2007 | Eliasen et al. |
| 2007/0265700 A1 | 11/2007 | Eliasen et al. |
| 2007/0293943 A1 | 12/2007 | Quinn |
| 2008/0086164 A1 | 4/2008 | Rowe |
| 2008/0109069 A1 | 5/2008 | Coleman et al. |
| 2008/0119889 A1 | 5/2008 | Kusleika |
| 2008/0125861 A1 | 5/2008 | Webler et al. |
| 2008/0147180 A1 | 6/2008 | Ghione et al. |
| 2008/0288061 A1 | 11/2008 | Maurer et al. |
| 2009/0030510 A1 | 1/2009 | Ho |
| 2009/0131849 A1 | 5/2009 | Maurer et al. |
| 2009/0240326 A1 * | 9/2009 | Wilson ................. A61F 2/2427 623/2.11 |
| 2010/0161043 A1 | 6/2010 | Maisano et al. |
| 2010/0298929 A1 | 11/2010 | Thornton et al. |
| 2010/0324668 A1 | 12/2010 | Maurer et al. |
| 2011/0022164 A1 * | 1/2011 | Quinn ................. A61L 31/145 623/2.11 |
| 2011/0077733 A1 | 3/2011 | Solem |
| 2011/0124950 A1 | 5/2011 | Foster |
| 2011/0282127 A1 | 11/2011 | Cui |
| 2012/0209377 A1 | 8/2012 | MacHold et al. |
| 2013/0041459 A1 | 2/2013 | Wilson et al. |
| 2013/0053882 A1 | 2/2013 | Hocking et al. |

* cited by examiner

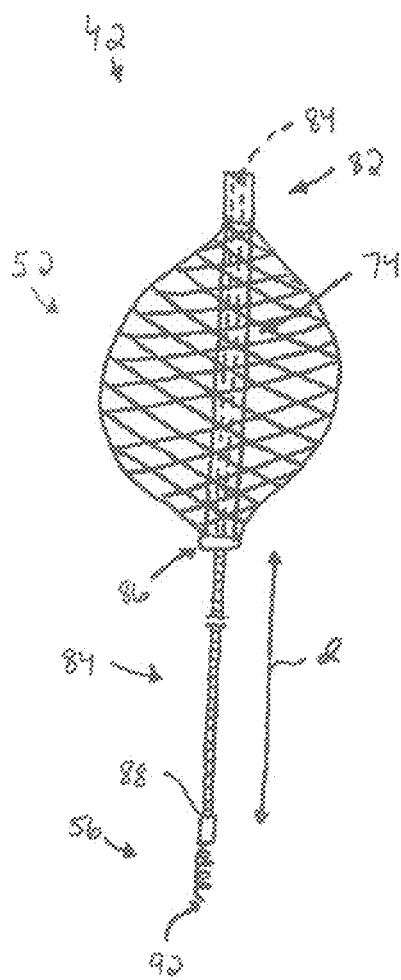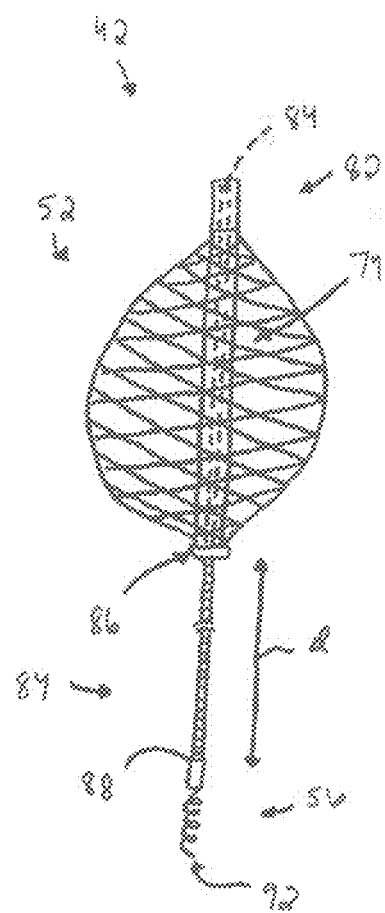
Fig. 4A
Fig. 4B

SYSTEMS AND METHODS FOR TREATING A REGURGITANT HEART VALVE

RELATED APPLICATIONS

This application is a continuation-in-part of U.S. patent application Ser. No. 14/883,819, filed Oct. 15, 2015, which is a divisional application of U.S. Pat. No. 9,161,837, filed Jul. 27, 2012, which claims the benefit of U.S. Provisional Patent Application Ser. No. 61/512,170, filed Jul. 27, 2011. This application also claims the benefit of U.S. Provisional Patent Application Ser. No. 62/492,379, filed May 1, 2017. The entirety of each of the foregoing applications is hereby incorporated by reference for all purposes.

TECHNICAL FIELD

The present disclosure relates generally to systems and methods for treating and improving the function of dysfunctional heart valves and, more particularly, to a selectively adjustable system that passively assists in closing the native heart valve leaflets to improve valve function of a regurgitant heart valve.

BACKGROUND

Normal mitral or tricuspid valve opens when the ventricle relaxes (diastole) allowing blood to flow from the atrium to the decompressed ventricle. When the ventricle contracts (systole), the increase in pressure causes the valve to close, preventing blood from leaking into the atrium and assuring that all of the blood leaving the ventricle (the stroke volume) is ejected through the valve (either aortic or pulmonary) into the body.

Proper function of the valve is dependent on a complex interplay between the annulus leaflets and subvalvular apparatus. In this interplay, the coaptation zone of the valve is critical to valve competency in closing and preventing regurgitation. The zone of coaptation is represented by a gently curved line between the anterior and posterior leaflets (and septal leaflet for tricuspid valve). As the dilation of the ventricle occurs the leaflets are pulled away from each other preventing the parts to properly co-apt, thus creating regurgitation. Whether it is the mitral or tricuspid valve, the mechanism of functional valve regurgitation is the same, which is due to negative heart remodeling or more specifically dilatation.

SUMMARY

The present disclosure relates generally to systems and methods for treating and improving the function of dysfunctional heart valves and, more particularly, to a selectively adjustable system that passively assists in closing the native heart valve leaflets to improve valve function of a regurgitant heart valve.

One aspect of the present disclosure relates to a system for treating regurgitation of blood through a diseased heart valve having at least two leaflets. The system can include an implantable, lollipop-shaped device and an adjustment mechanism. The device can have a proximal end portion, a distal end portion, and an intermediate portion extending between the proximal and distal end portions. The intermediate portion can include an expandable occluding member having a selectively adjustable diameter. At least a portion of the occluding member can include a biocompatible layer attached thereto. The distal end portion can include an anchoring member for securing the device in a heart chamber containing the diseased heart valve. The adjustment member can include an elongated body having a proximal control end and a distal connecting end that is operatively connected to the proximal end portion of the device. Operation of the adjustment member, after implantation of the device in the diseased heart valve, can cause the diameter of the occluding member to increase or decrease so that, during at least a portion of the cardiac cycle, at least one of the heart leaflet coapts with a portion of the occluding member to mitigate or prevent regurgitation of blood through the diseased heart valve.

Another aspect of the present disclosure relates to a method for treating regurgitation of blood through a diseased heart valve having at least two leaflets. One step of the method can comprise providing a system. The system can comprise an implantable, lollipop-shaped device and an adjustment member. The device can have a proximal end portion, a distal end portion, and an intermediate portion extending between the proximal and distal end portions. The intermediate portion can include an expandable occluding member having a selectively adjustable diameter, at least a portion of the occluding member also including a biocompatible layer attached thereto. The distal end portion can include an anchoring member for securing the device in a heart chamber containing the diseased heart valve. The adjustment member can include an elongated body having a proximal control end and a distal connecting end and being operatively connected to the proximal end portion of the device. Next, the anchoring member can be secured in a heart chamber containing the heart valve. The adjustment member can then be operated so that at least a portion of the occluding member is securely positioned within the diseased heart valve. The adjustment member can be further operated to increase or decrease the diameter of the occluding member so that at least one of the diseased heart valve leaflets coapts with the occluding member during the cardiac cycle.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIGS. 4A-B are schematic illustrations showing different configurations of an anchoring line comprising the system in FIG. 1;

DETAILED DESCRIPTION

Definitions

Figure 1:
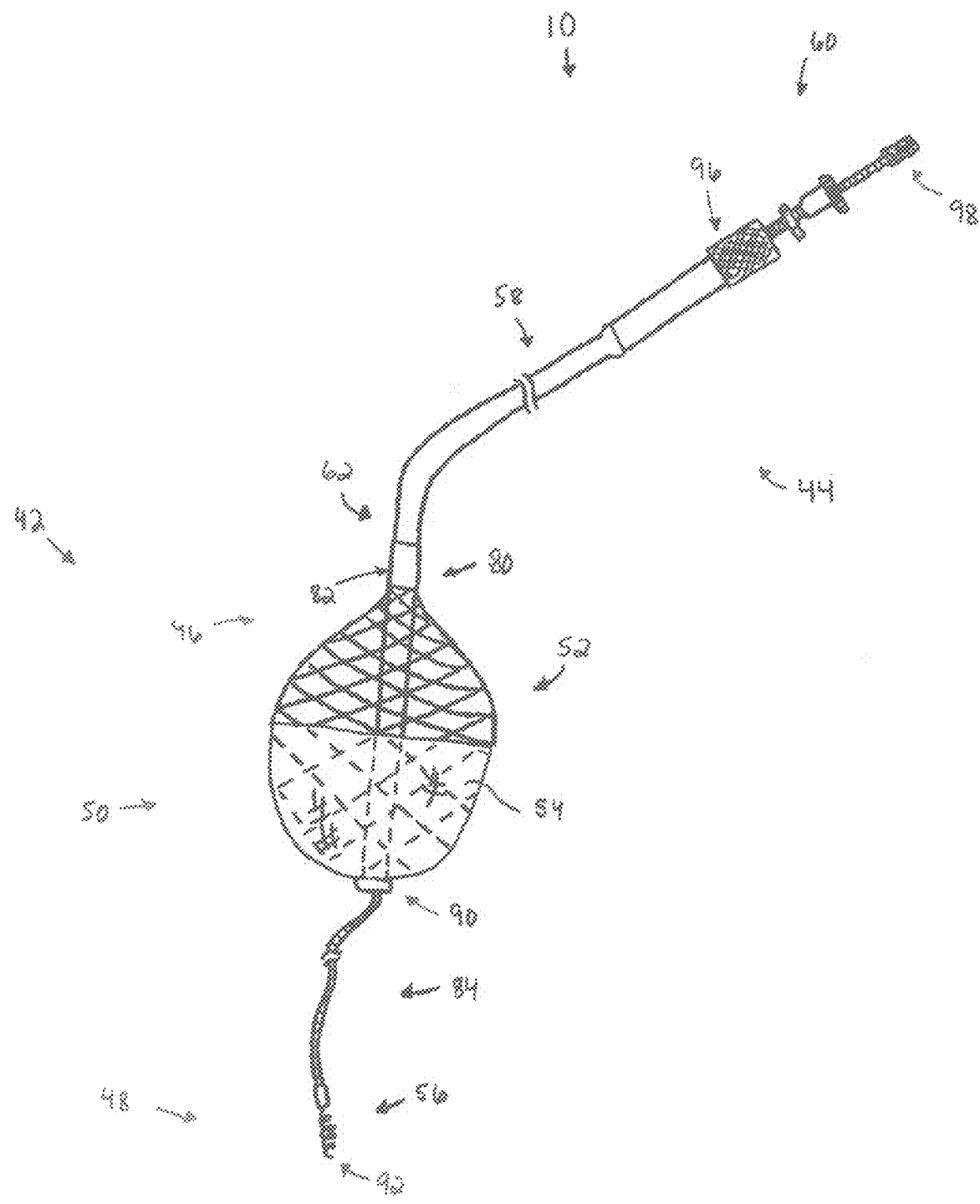
FIG. 1 is a schematic illustration showing a system for treating regurgitation of blood through a diseased heart valve constructed in accordance with one aspect of the present disclosure.

Unless defined otherwise, all technical and scientific terms used herein have the same meaning as is commonly understood by one of skill in the art to which the present disclosure pertains.

In the context of the present disclosure, the term "subject" can be used interchangeably with the term "patient" and refer to any organism including, but not limited to, human beings, pigs, rats, mice, dogs, goats, sheep, horses, monkeys, apes, farm animals, livestock, rabbits, cattle, etc.

As used herein, the term "in electrical communication" can refer to a first element or component that is directly or indirectly coupled to a second element or component by at least one conducting medium (e.g., a wire).

As used herein, the term "in fluid communication" can refer to a communication between two sections, components, or features of the systems of the present disclosure. In some instances, this communication may be a direct connection or a direct path between two sections, components, or features or, alternatively, may include one or more intervening sections in the path between two sections, components, or features of the systems of the present disclosure.

As used herein, the term "operatively connected" can refer to an arrangement of elements or components that establishes either a static connection or a kinetic interaction between the recited elements or components, either by direct attachment of the elements or components together or by connection of the elements or components through one or more intervening elements or components. "Static connection" can refer to an arrangement where one element or component and at least a second element or component does not move with respect to one another. "Kinetic interaction" can refer to an arrangement where one element or component may move with respect to at least a second element or component with such movement controlled by the connection of the element(s) or component(s) and, if applicable, any intervening element(s) or component(s).

As used herein, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "directly adjacent" another feature may have portions that overlap or underlie the adjacent feature, whereas a structure or feature that is disposed "adjacent" another feature may not have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of a device in use or operation, in addition to the orientation depicted in the figures. For example, if a device in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

Overview

The present disclosure relates generally to systems and methods for treating and improving the function of dysfunctional heart valves and, more particularly, to a selectively adjustable system that passively assists in closing the native heart valve leaflets to improve valve function of a regurgitant heart valve. Implantable devices for passively assisting with heart valve leaflet coaptation are known in the art. Such devices are typically implanted following imaging studies of the pertinent cardiac structures and/or upon visual inspection (e.g., by a surgeon during an open chest procedure). Either upon implantation or shortly thereafter, however, optimal valve leaflet coaptation may be lost due to unaccounted for variances in device construction and/or heart movement. As described below, one aspect of the present disclosure provides a system 10 (FIG. 1) whose position and dimensions can advantageously be selectively adjusted before, during, and after implantation to facilitate optimal valve leaflet coaptation therewith and, thus, ensure that regurgitation of blood through the heart valve is minimized or prevented.

Further applications and advantages of the present disclosure are discussed below.

Figure 2:
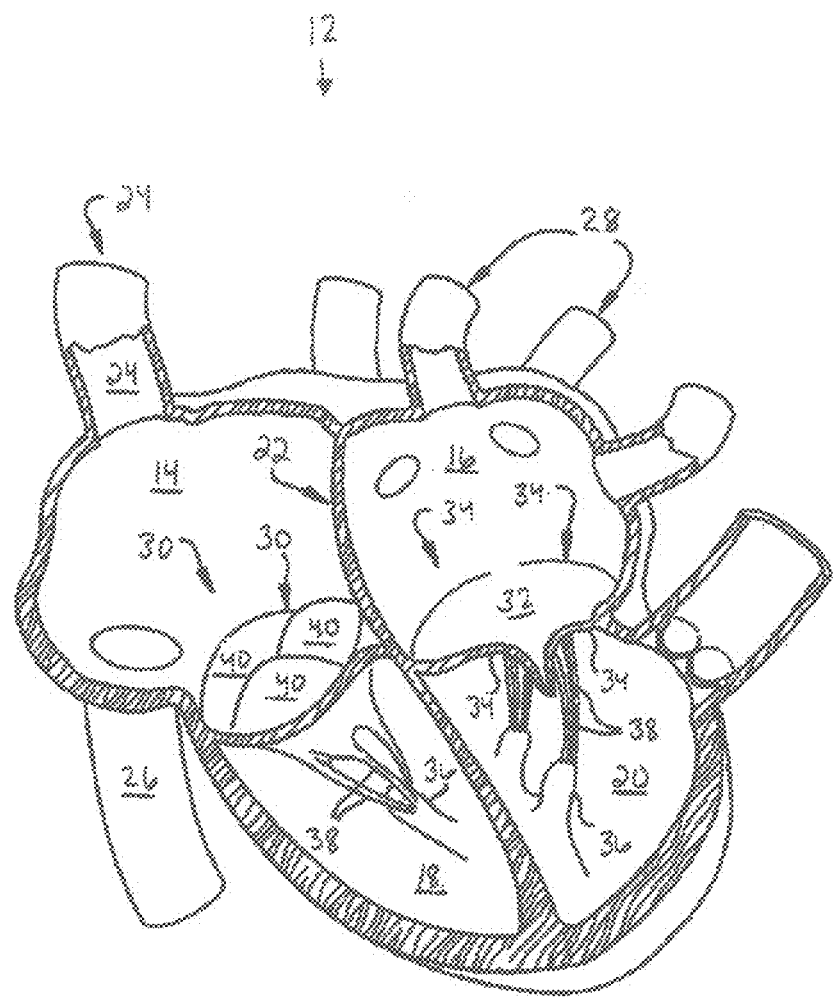
FIG. 2 is a cross-sectional schematic view of a human heart.

Reference shall be made herein to FIG. 2, which schematically illustrates a human heart 12. The heart 12 includes the right and left atria 14 and 16, and the right and left ventricles 18 and 20. The right and left atria 14 and 16 are divided by the interatrial septum 22. The thin-walled right atrium 14 receives deoxygenated blood from the superior vena cava 24, the inferior vena cava 26, and from the coronary sinus (not shown). The thin-walled left atrium 16 receives oxygenated blood from pulmonary veins 28. The right and left ventricles 18 and 20 pump oxygenated and deoxygenated blood, respectively, throughout the body, and the pocket-like semilunar pulmonary valve (not shown) and the aortic valve (not shown) prevent reflux into the ventricles. Atrial blood is pumped through the atrioventricular orifices, guarded by the tri-leaflet tricuspid valve 30 on the right side of the heart 12, and the bi-leaflet mitral valve 32 on the left side of the heart. The free edges of the mitral leaflets 34 are attached to the papillary muscles 36 in the right and left ventricles 18 and 20 by chordae tendineae 38. Similarly, the free edges of the tricuspid leaflets 40 are attached to the papillary muscles 36 in the right and left ventricles 18 and 20 by chordae tendineae 38.

Systems

One aspect of the present disclosure can include a system 10 (FIG. 1) for treating regurgitation of blood through a diseased heart valve having at least two leaflets. The system 10 can comprise an implantable, lollipop-shaped device 42 and an adjustment member 44. The device 10 can have a proximal end portion 46, a distal end portion 48, and an intermediate portion 50 extending between the proximal and distal end portions. The intermediate portion 50 can include an expandable occluding member 52 having a selectively adjustable diameter. At least a portion of the occluding member 52 can include a biocompatible layer 54 attached thereto. The distal end portion 48 can include an anchoring member 56 for securing the device 42 in a heart chamber containing the diseased heart valve. The adjustment member 44 can include an elongated body 58 having a proximal control end 60 and a distal connecting end 62 that is operatively connected to the proximal end portion 46 of the device 10. Operation of the adjustment member 44, after implantation of the device 10 in the diseased heart valve, can cause the diameter of the occluding member 52 to increase or decrease so that, during at least a portion of the cardiac cycle, at least one of the heart leaflet coapts with a portion of the occluding member to mitigate or prevent regurgitation of blood through the diseased heart valve.

In some instances, the occluding member 52 can have an outer surface 64 for coapting with at least one heart valve leaflet. As described below, the occluding member 52 assists in closing a diseased heart valve to prevent regurgitation by increasing the coaptation area and/or decreasing the coaptation depth of the valve leaflets. Increasing coaptation of the valve leaflets is generally accomplished by placing the occluding member 52 in a regurgitant valve orifice, thereby providing a surface against which the valve leaflets may abut (i.e., coapt) to close the valve during systole. The occluding member 52 assists in substantially closing the diseased heart valve without altering the shape of the valve annulus and/or repositioning the papillary muscles 36. The presence of the occluding member 52 will block regurgitant blood flow through the diseased heart valve during systole as the leaflets abut against the outer surface 64 of the occluding member 52. In other words, the occluding member 52 "plugs" the regurgitant valve orifice during systole to hinder or prevent blood from leaking through the diseased heart valve.

In some instances, the foregoing description of the occluding member 52 relates to a "compliant" occluding member as the occluding member is allowed to flex and re-shape itself in response to external forces applied by the valve leaflets. Alternatively, in other instances, the foregoing description of the occluding member 52 relates to a "non-compliant" occluding member whereby the occluding member does not flex or re-shape when implanted in a subject. Rather, a material or combination of materials (e.g., Dacron, bovine pericardium, hydrogel swellable materials, etc.) is/are attached (e.g., directly attached) to the occluding member 52 (e.g., covering all or only a portion of an inner and/or outer surface thereof) so that the total open surface area, where the valve is opened, is reduced. In one example, the non-compliant occluding member 52 can include an amount of heart leaflet pericardium (e.g., covering all or only a portion of an inner and/or outer surface thereof) sufficient to create a device 42 having overall rigid configuration that stops or prevents back-flow into the atrium (right or left atrium, depending upon the particular diseased heart valve being treated) when the heart leaflets coapt with the occluding member.

The occluding member 52 can be defined by a first end 66, an opposite second end 68, and a center portion 70 located between the first and second ends. The occluding member 52 can be made of any one or combination of materials. As shown in FIG. 1, for example, the occluding member 52 can have a mesh configuration and be formed from a plurality of wires. Such wires can be made, for example, from stainless steel, titanium alloys, cobalt-chrome alloys, Nitinol, and the like. In one example, the occluding member 52 can be made of braided Nitinol wire comprising different PPM (picks-per-inch) ranges. Where a Nitinol braid is constructed, the density of the braid can be specified as coarse or fine through the addition or subtraction of wires during the braiding process. The end result is an occluding member 52 with a different compliance. It will be appreciated that the wire used to create the occluding member 52 can play a role in controlling the stiffness of the occluding member. For example, low diameter, surface area, and cross-sectional geometry of a Nitinol wire can create a more compliant occluding member 52, whereas a larger wire can create a stiffer occluding member.

In some instances, the occluding member 52 can be coated with a heparin coating to prevent thrombogenicity of the device in the blood flow as the shear stresses are changed due to modeling of the ventricle.

Figures 3A, 3B:
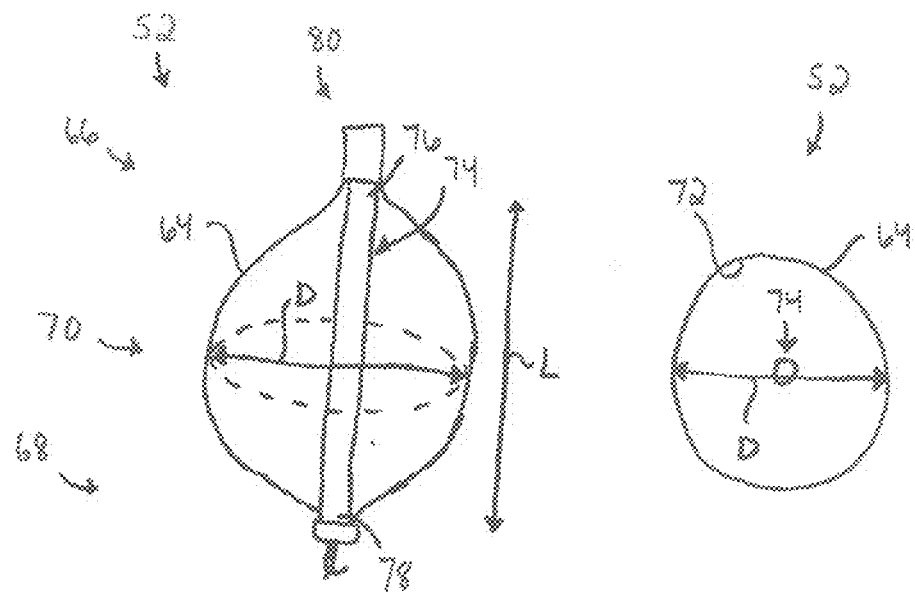
FIG. 3A is a magnified schematic illustration of an occluding member comprising the system in FIG. 1 (cross-hatching omitted for clarity)
FIG. 3B is a top view showing the diameter D of the occluding member in FIG. 3A.
Figures 3C, 3D:
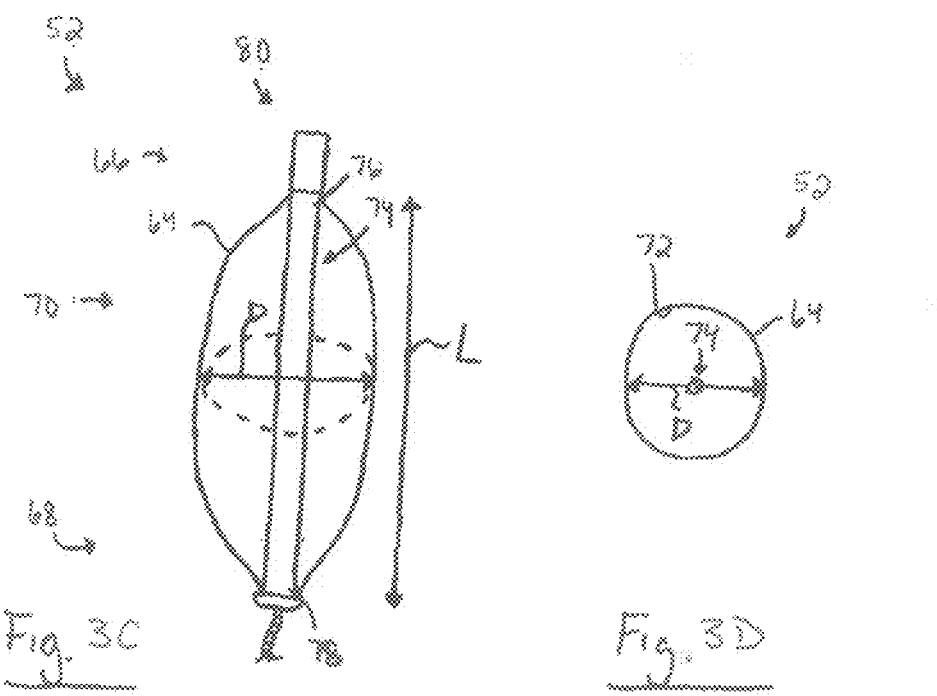
FIG. 3C is a magnified schematic illustration showing an alternative configuration of the occluding member in FIG. 3A (cross-hatching omitted for clarity)
FIG. 3D is a top view showing the diameter D of the occluding member in FIG. 3C.

The occluding member 52 is collapsible to a low profile. For example, the occluding member 52 can be configured to collapse from a first profile to a second smaller profile (e.g., 3 Fr to 12 Fr). The occluding member 52 can include a diameter D (FIGS. 3A-B) that extends between oppositely disposed inner surfaces 72 at the center portion 70 of the occluding member. As explained in more detail below, the diameter D can be selectively increased or decreased to vary the configuration of the occluding member 52 from a generally bulbous shape (FIG. 3A) to a generally ovoid shape (FIG. 3C). The ability to selectively increase or decrease the diameter D of the occluding member 52, and thus the surface area available for coaptation, is advantageous because the cross-sectional area of the occluding member can be adjusted in real-time to optimize leaflet coaptation with the outer surface of the occluding member.

As shown in FIG. 1, the occluding member 52 can additionally or optionally include a biocompatible layer 54 to stop blood flow from moving from ventricle to atrium outside its appropriate cardiac cycle. The biocompatible layer 54 can comprise one or a combination of materials, such as PTFE, Teflon, ePTFE, Dacron, a hydrogel, etc. The biocompatible layer 54 can span the entire outer surface 64 of the occluding member 52 or just a portion of the outer surface so as to achieve a seal against the open valve aperture when the valve leaflets close. The biocompatible layer 54 can extend circumferentially about the occluding member 52 between the center portion 70 and the second end 68 thereof. The biocompatible layer 54 can extend about all or only a portion of the outer surface 64, the inner surface 72, or both. If the biocompatible layer 54 is attached to the inner surface 72, the occluding member 52 can be made of a fine wire mesh having a density sufficient to prevent any material embolization from the occluding member to the lungs. If the biocompatible layer 54 is attached to the outer surface 64, the occluding member 52 can be made of a coarse wire mesh having a density sufficient to sew the layer on the occluding member and provide the appropriate occlusion performance. The biocompatible layer 54 can be secured to the occluding member 52 using any known attachment means, such as medical sutures. The biocompatible layer 54 can also promote proper leaflet coaptation with the occluding member 52 by preventing undesirable sticking or adherence of the valve leaflets to the occluding member during the cardiac cycle.

The occluding member 52 (FIGS. 3A-D) can additionally or optionally include a hollow tube member 74 having first and second ends 76 and 78. The tube member 74 can extend axially between the first and second ends 66 and 68 of the occluding member 52. The tube member 74 can be defined by a length L that can be selectively increased or decreased. As described in more detail below, the length L of the tube member 74 can be selectively decreased, which increases the diameter D of the occluding member 52 and imparts the occluding member with a generally bulbous shape. The length L of the tube member 74 can alternatively be selectively increased, which decreases the diameter D of the occluding member 52 and imparts the occluding member with an ovoid shape. The tube member 74 can be made of any one or combination of biocompatible and resiliently flexible materials, such as a polymer-based material capable of providing desirable mechanical and fatigue properties.

The first end 66 of the occluding member 52 and the first end 76 of the tube member 74 can be secured at the proximal end portion 46 of the device 42 by a connecting mechanism 80 (not shown in detail). The connecting mechanism 80 can include a cylindrical cap or tube 82, as well as an associated mechanism (not shown) for connecting to the adjustment member 44. Control over the shape of the occluding member 52 can be exerted through elongation of its first and second ends 66 and 68, as depicted in FIGS. 3A-D. In some instances, elongation can be done through an embedded leadscrew (not shown) where the proximal end 66 is anchored as a reference point and the second end 68 is moving when the leadscrew is turned clockwise or counter-clockwise. In other instances, 3 or more bars (not shown) operatively connected with cams (not shown) inside of the occluding member 52 can allow for specific shape control of the occluding member.

In another aspect, the device 42 can include at least one sensor (not shown) attached thereto. For example, one or more sensors can be attached (e.g., directly attached) to the occluding member 52 (e.g., on an interior or exterior surface thereof) and/or the threaded wire 84. The sensor(s) can be configured to detect one or more of intra-atrial pressure, intra-ventricular pressure, blood flow and temperature. For example, one or more sensors (e.g., pressure sensors) can be attached to the occluding member 52 to measure differential pressure during systole and diastole as a means for understanding the performance of the system 10. Detection of a low differential pressure may indicate that the device 42 (e.g., the occluding member 52) is not properly coapting with the heart valve leaflets and needs adjustment. Detection of a high differential pressure may indicate that the device 42 (e.g., the occluding member 52) is properly coapting with the heart valve leaflets and does not need adjustment. In some instances, pressure sensing can be intermittently or continuously monitored and transmitted to a physician or caregiver for analysis.

Referring to FIGS. 4A-B, the distal end portion 48 of the device 42 can include a threaded wire 84 having first and second ends 86 and 88. The threaded wire 84 can extend through the tube member 74 and include an anchoring member 56 for securing the device 42 in a heart chamber containing the diseased heart valve. The threaded wire 84 can also extend through a collar 90 having a threaded aperture (not shown). The threaded wire 84 can extend a distance d between the collar 90 and the anchoring member 56. As described in more detail below, the distance d can be selectively increased or decreased to vary the position of the occluding member 52 relative to the diseased heart valve. The occluding member 52 can be configured to ride along the threaded wire 84 to a desired position so the occluding member is in the plane of the heart valve. This adjustment advantageously provides a new degree-of-freedom and ease of use in placing the occluding member 52 within three-dimensional cardiac anatomy. Within translational limits, the occluding member 52 can be configured to move up or down along the threaded wire 84 to adjust its position and thereby account for the influence of blood movement between atrium and ventricle. Although not shown, the device 42 can additionally include one or more springs to provide mechanical energy and act as forces to facilitate the coaptation process.

The anchoring member 56 can have any construction or configuration to facilitate secure attachment and implantation of the device 42. As shown in FIGS. 4A-B, the anchoring member 56 can have a spiral or coiled shape and includes a sharpened distal tip 92. The spiral or coiled shape of the anchoring member 56 facilitates entry and subsequent embedding of the anchoring portion in heart tissue surrounding the diseased heart valve. It will be appreciated that the anchoring member 56 can have other configurations besides the one shown in FIGS. 4A-B. For example, the anchoring member 56 can have a clip-like (not shown) or barb-shaped configuration (not shown). As described below, the threaded wire 84 and the compressible tube member 74 collectively form an adjustment mechanism that enables selective adjustment of the position and diameter D of the occluding member 52.

It will be appreciated that the system 10 may include at least one radiographically opaque marking (not shown) to facilitate positioning of the device 42 in a diseased heart valve. The radiographically opaque marking may be located on the occluding member 52 or, alternatively, at any other portion of the device 42. The radiographically opaque marking can be any one or combination of materials or devices with significant opacity. Examples of such radiographically opaque markings include, but are not limited to, a steel mandrel sufficiently thick to be visible on fluoroscopy, a tantalumlpolyurethane tip, a gold-plated tip, bands of platinum, stainless steel or gold, soldered spots of gold, and polymeric materials with a radiographically opaque filter, such as barium sulfate.

Referring again to FIG. 1, the adjustment member 44 of the system 10 can include an elongated body 58 having a proximal control end 60 and a distal connecting end 62 that is operatively connected to the proximal end portion 46 of the device 42. The distal connecting end 62 is adapted to mate with the connecting mechanism 80 of the device 42. The elongated body 58 comprises a shaft that extends between the proximal control end 60 and the distal connecting end 62. In one example, the proximal control end 60 can include a first handle member 94 for controlling the position of the occluding member 52 relative to the diseased heart valve, and a second handle member 96 for controlling the diameter D of the occluding member. Further details of the proximal control end 60 are disclosed in U.S. patent application Ser. No. 13/559,900, filed Jul. 27, 2012, to Kapadia. Although knobs are shown as being axially stacked or aligned in FIG. 1, it will be appreciated that the knobs can alternatively be non-axially stacked or aligned.

In some instances, the shaft comprising the adjustment member 44 can be braided or non-braided. The shaft can be coated with an anti-thrombogenic agent, an anti-microbial agent, or a combination thereof. In one example, the shaft can be configured to exert a downward force on the device 42, when implanted in a subject, to ensure that the leaflets coapt with the occluding member 52 during at least a portion of the cardiac cycle. In another example, the shaft can comprise one or more coils (not shown) having a diameter approximately equal to a diameter of a subclavian vein such that the one or more coils exert a radial force against a wall of the subclavian vein to anchor of the device 42 in the diseased heart valve. In such instances, the coil(s) can exert a radial force against the vessel wall in the same fashion as a stent for the purpose of anchoring the device 42. The purpose is to store mechanical energy that can be utilized to anchor the system 10 in place or used for another purpose.

In another aspect, the adjustment member 44 can include a release mechanism (e.g., a button) (not shown) that, when actuated, separates the adjustment member from the device 42 so that the device remains implanted in the diseased heart valve. In such cases, the adjustment member 44 can serve as a delivery system for the device 42. As such, the adjustment member 44 can be configured to deflect and curve through the vasculature, regardless of whether subclavian vein or groin access is used. The adjustment member 44 can then be used to adjust the shape of the occluding member 52 to obtain adequate hemodynamics and low regurgitation grade before releasing the device 42 as an implant. One skilled in the art will appreciate that the adjustment member 44 can have one or a combination of magnet or key-slot mechanisms to allow latching and retrieval of the device 42 in case of ventricular positive remodeling. Thus, after a positive remodeling of the ventricle or any requirements for a new procedure, the device 42 can be percutaneously retrieved and removed, thereby rendering the device an implant of a temporary nature. However, it will be appreciated that the device 42 and/or system 44 can be permanently implanted if there is no evidence of positive remodeling.

Figure 5:
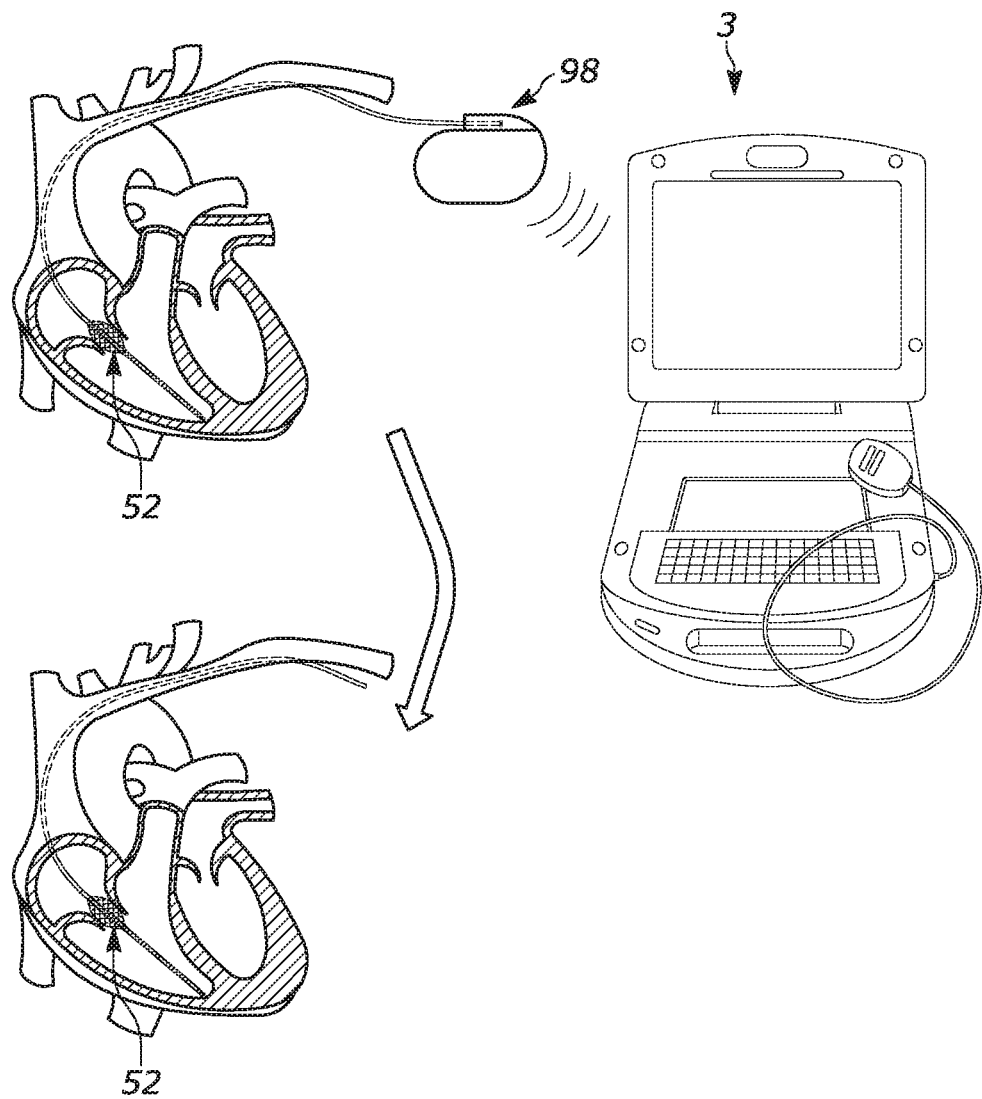
FIG. 5 is a schematic illustration showing a system for treating regurgitation of blood through a diseased heart valve constructed in accordance with another aspect of the present disclosure.
Figure 6:
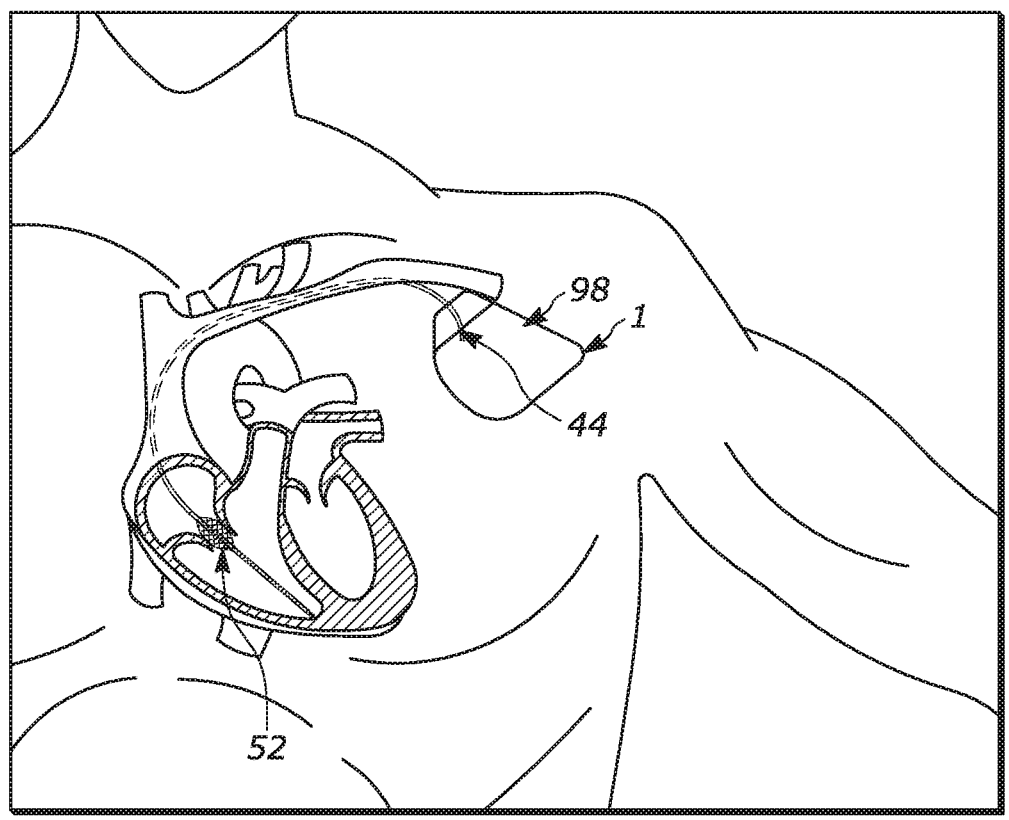
FIG. 6 is a schematic illustration showing a system for treating regurgitation of blood through a diseased heart valve constructed in accordance with another aspect of the present disclosure.
Figure 7:
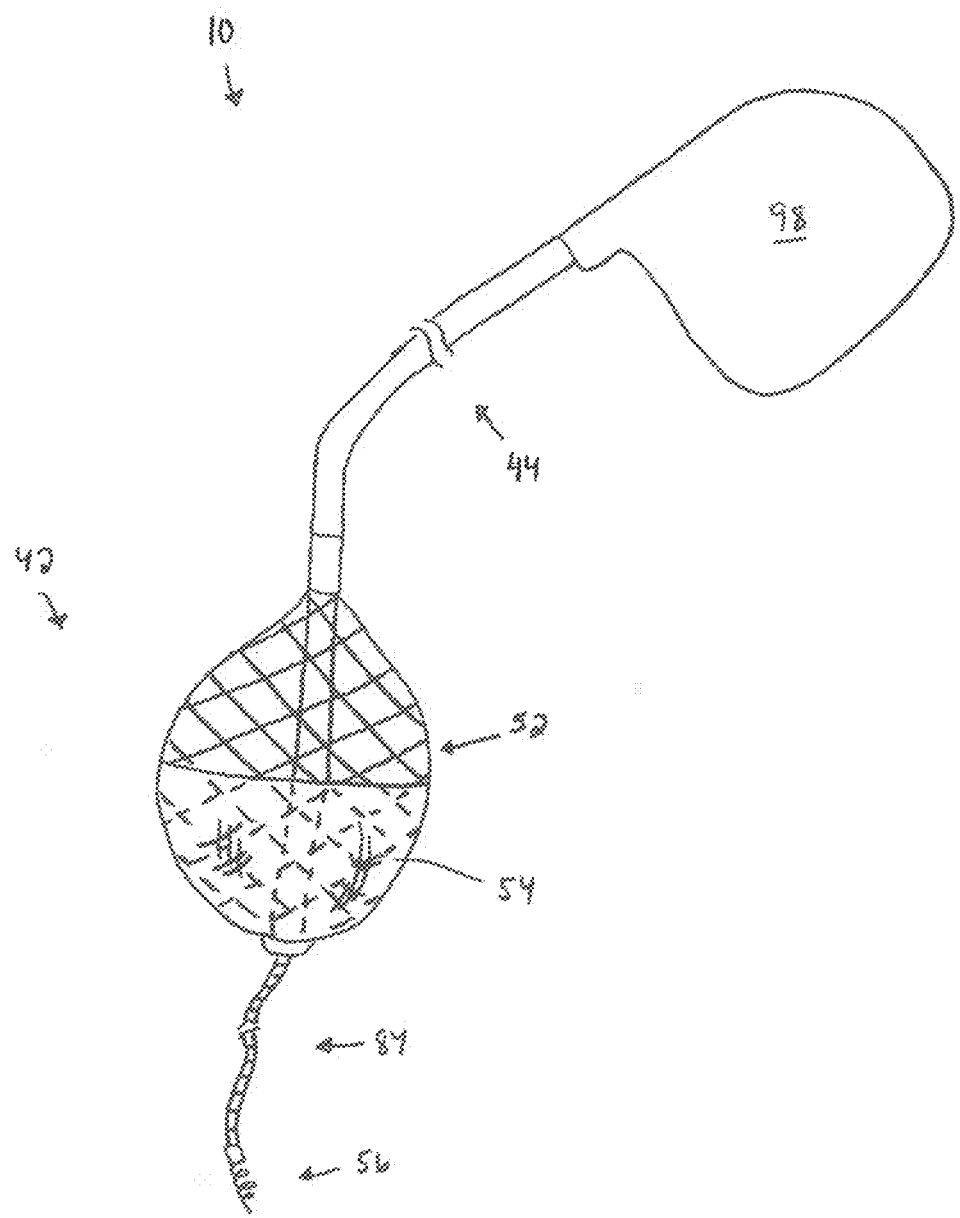
FIG. 7 is a schematic illustration showing a system for treating regurgitation of blood through a diseased heart valve constructed in accordance with another aspect of the present disclosure.

In another aspect, the system 10 can include an electronic control device 98 (FIG. 7) in electrical communication with the adjustment member 44 and/or the device 42. In some instances, the electronic control device 98 can be configured to automatically (e.g., by programming) adjust the size and/or position of the occluding member 52 relative to the diseased heart valve based on one or more feedback parameters. In one example, the electronic control device 98 can comprise a pacemaker including at least one implantable lead (not shown). In this configuration, the adjustment member 44 and/or the device 42 can be mechanized and electrically controlled with one or more feedback mechanisms (e.g., sensors) to replicate functions previously described with respect to the proximal control end 60. For example, the electronic control device 98 can automatically control and adjust the shape and/or position of the occluding member 52 based on one or more detected feedback parameters (e.g., differential pressure, temperature, blood flow, etc.). In some instances, the electronic control device 98 can be remotely controlled using a computer 3 (FIG. 5) or a handheld digital device (e.g., a cell phone, tablet, etc.) (not shown). In one example, the device 42 can be implanted alongside a pacemaker lead while the electronic control device 98 is implanted within a subcutaneous pocket 1 (FIG. 6). In other words, the occluding member 52 and the adjustment member 44 share the same percutaneous pocket 1 as the pacemaker. This configuration may be especially advantageous in patients with a pacemaker lead that have limited options for intervention as the lead might interfere with future devices.

Methods

Another aspect of the present disclosure can include a method for treating regurgitation of blood through a diseased tricuspid valve 100. The method can be performed using the system 10 illustrated in FIG. 1. The system 10, for example, can comprise a device 42 and an adjustment member 44 that are similarly or identically constructed as the device and adjustment member described above.

Figure 8:
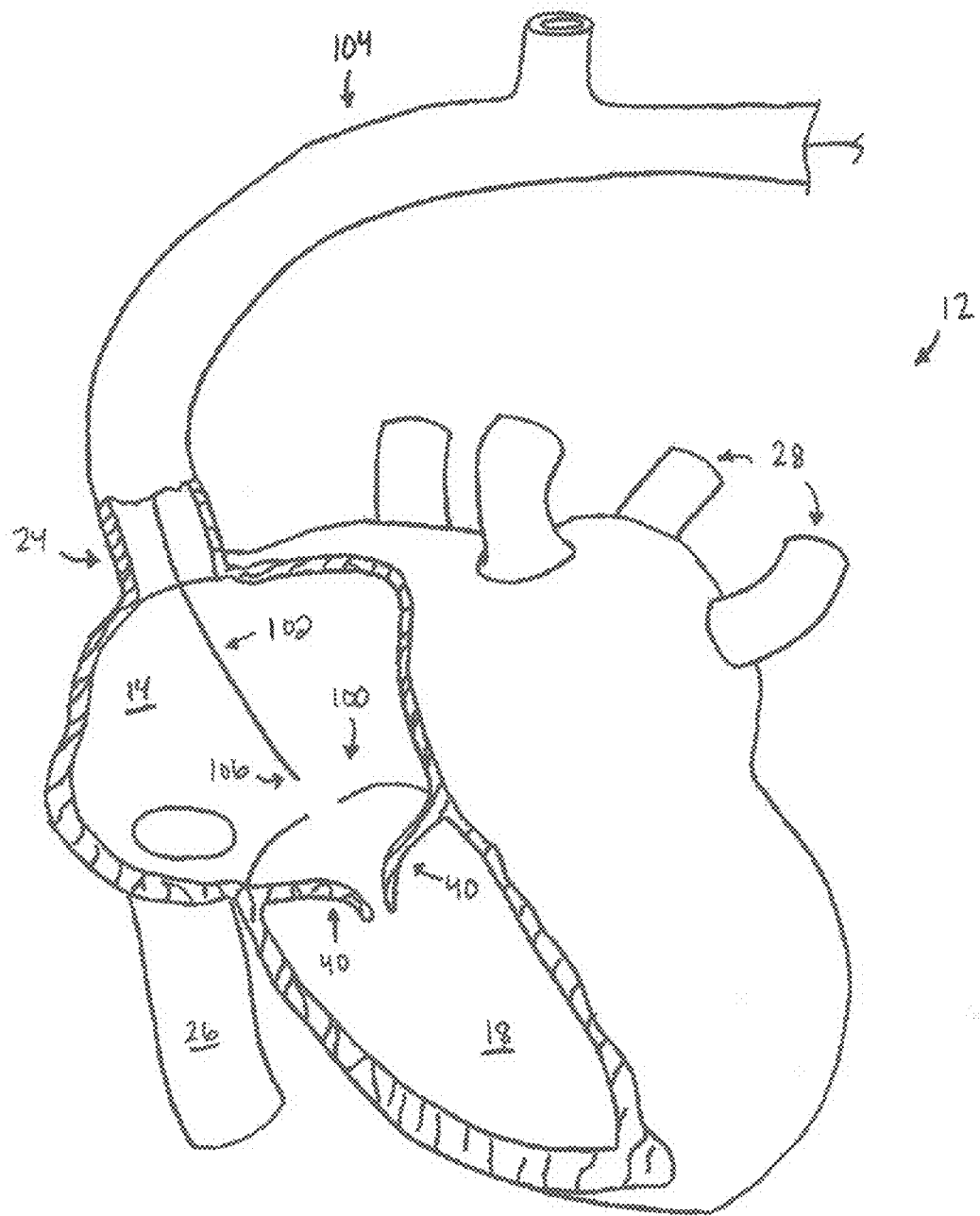
FIG. 8 is a cross-sectional view showing a guidewire extending through a subclavian vein, across the superior vena cava, and into the right atrium.

A percutaneous approach can be used to deliver the device 42 to the diseased tricuspid valve 100. To do so, a guidewire 102 is inserted into a venous access site, such as a patient's subclavian vein 104, jugular vein or femoral vein (not shown). Where the guidewire 102 is inserted into a subclavian vein 104, image guidance (e.g., fluoroscopy, ultrasound, magnetic resonance, computed tomography, or combinations thereof) can be used to steer through the guidewire through the subclavian vein, across the superior vena cava 24, and into the right atrium 14 (as shown in FIG. 8). It will be appreciated that other intra-vascular approaches to the tricuspid valve 100 can be used, such as through the groin (e.g., femoral vein) of a subject. In this case, all or only a portion of the adjustment member 44 can be implanted in a subcutaneous pocket (not shown) created in a thigh of the subject.

Once a distal end 106 of the guidewire 102 has reached the right atrium 14, the distal end may be hinged downward toward the diseased tricuspid valve 100. The guidewire 102 may then be urged through the diseased tricuspid valve 100 so that the distal end 106 enters the right ventricle 18. The guidewire 102 may next be positioned in the right ventricle 18 so that the guidewire is securely positioned within the superior vena cava 24, the right atrium 14, and the subclavian vein 104.

After the guidewire 102 is secured in the patient's heart 12, a catheter 108 (FIG. 9) may be passed over the guidewire and advanced into the right atrium 14. If it has not been done so already, the system 10 can be mated with a proximal end (not shown) of the guidewire 102. Next, an axial force is applied to the proximal control end 60 of the adjustment member 44 so that the device 42 is passed over the guidewire 102. The device 42 is advanced along the guidewire 102 until the device reaches a distal end portion 110 of the catheter 108.

Figure 9:
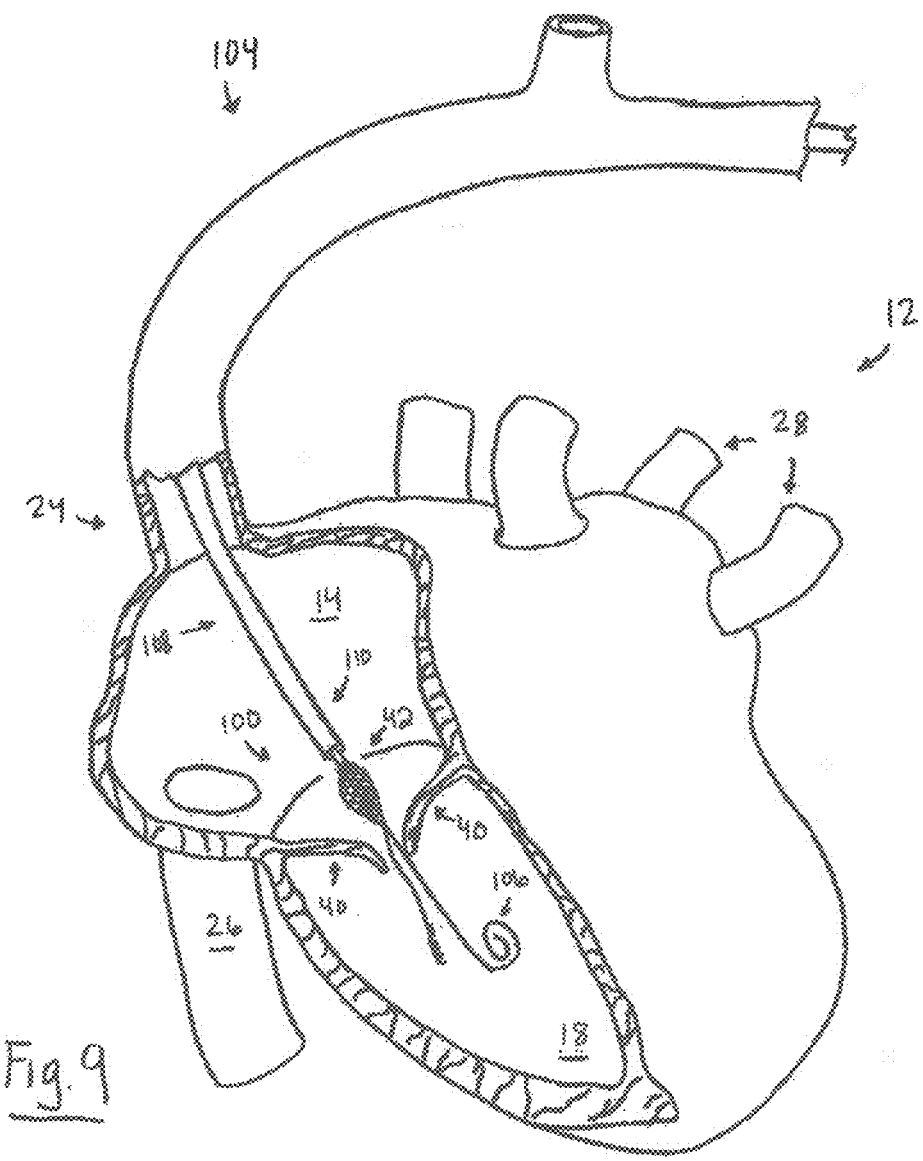
FIG. 9 is a cross-sectional view showing a device comprising the system of FIG. 1 partly deployed in a diseased tricuspid valve.

Upon reaching the distal end portion 110 of the catheter 108, the device 42 can be progressively freed from the catheter as shown in FIG. 9. As the device 42 is progressively freed from the catheter 108, the position of the device within the heart 12 can be monitored, controlled, and/or quality assured by imaging systems of various kinds. For example, X-ray machines, fluoroscopic machines, ultrasound, CT, MRI, PET, and other imaging devices may be used.

Once the device 42 is freed from the catheter 108, the device may be appropriately positioned in the heart 12. More particularly, the anchoring member 56 may be urged toward the wall of the right ventricle 18 until the sharpened tip 92 contacts the right ventricular wall (FIG. 10), and the anchoring member is positioned so that the occluding member 52 is at or slightly below the level of the tricuspid annulus. It will be appreciated that depending upon the location and geometry of the regurgitant tricuspid valve orifice, the occluding member 52 may be suspended at any one of a number of different positions. For example, the occluding member 52 may be positioned approximately level to the tricuspid annulus. Alternatively, the occluding member 52 may be positioned so that at least a portion of the occluding member is positioned below the free ends of the tricuspid valve leaflets 40.

Figure 10:
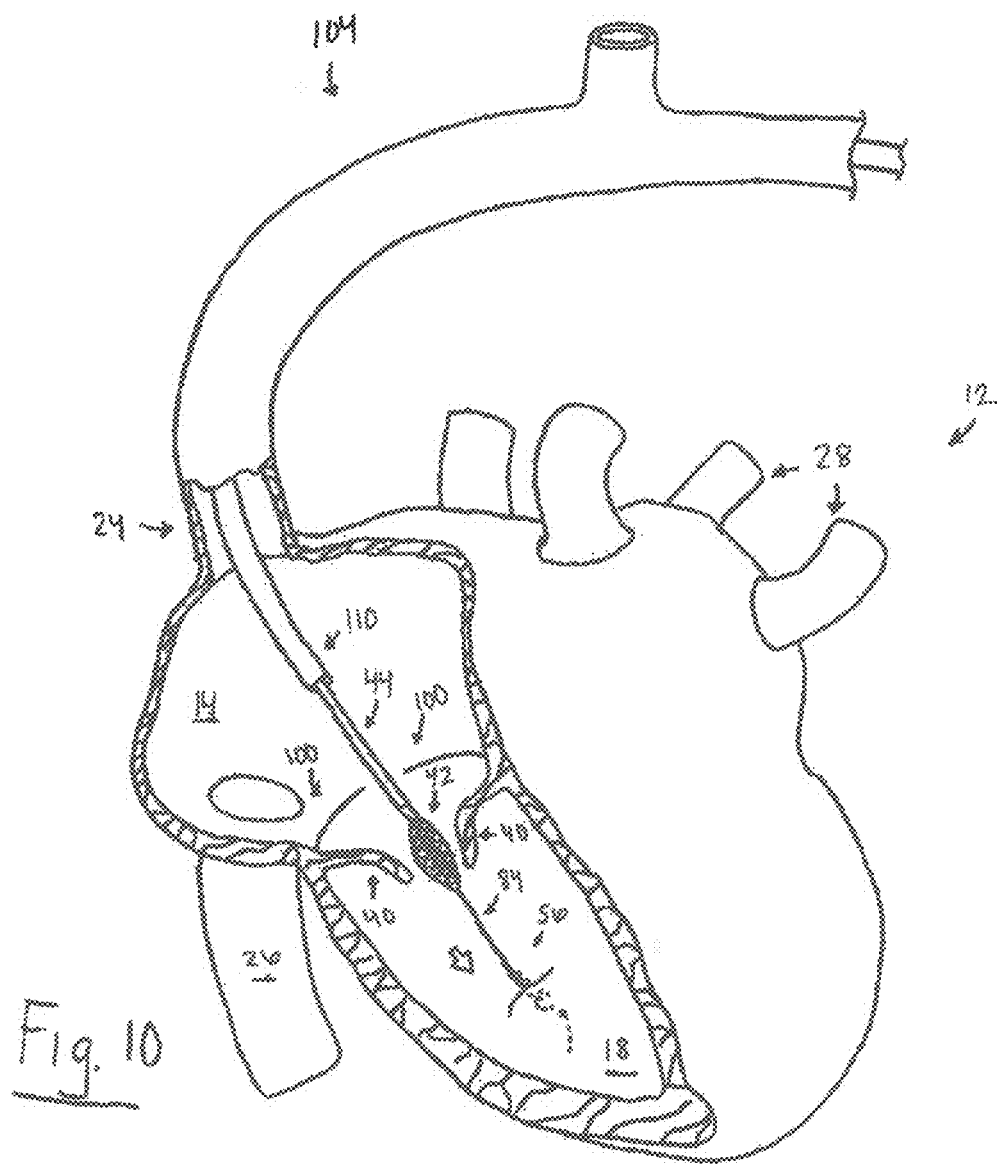
FIG. 10 is a cross-sectional view showing the device in FIG. 9 being anchored in the right ventricle.

The first handle member 94 of the proximal control end 60 can then be turned in clockwise manner, which causes the threaded wire 84 to be extruded from the collar 90 and force the sharpened tip 92 of the anchoring member 56 into the heart tissue (as indicated by the arrow in FIG. 10). The first handle member 94 can be operated (i.e., turned in clockwise manner) until the anchoring member 56 is substantially or entirely embedded within the right ventricular wall. If needed, the position of the occluding member 52 relative to the diseased tricuspid valve 100 can be adjusted. To move the occluding member 52 in a superior direction, for example, the first handle member 94 can be rotated in a counter-clockwise direction, which increases the distance d of the threaded wire 84. Conversely, the occluding member 52 can be moved in an inferior direction by rotating the first handle member 94 in a clockwise direction, which decreases the distance d of the threaded wire 84.

Figure 11:
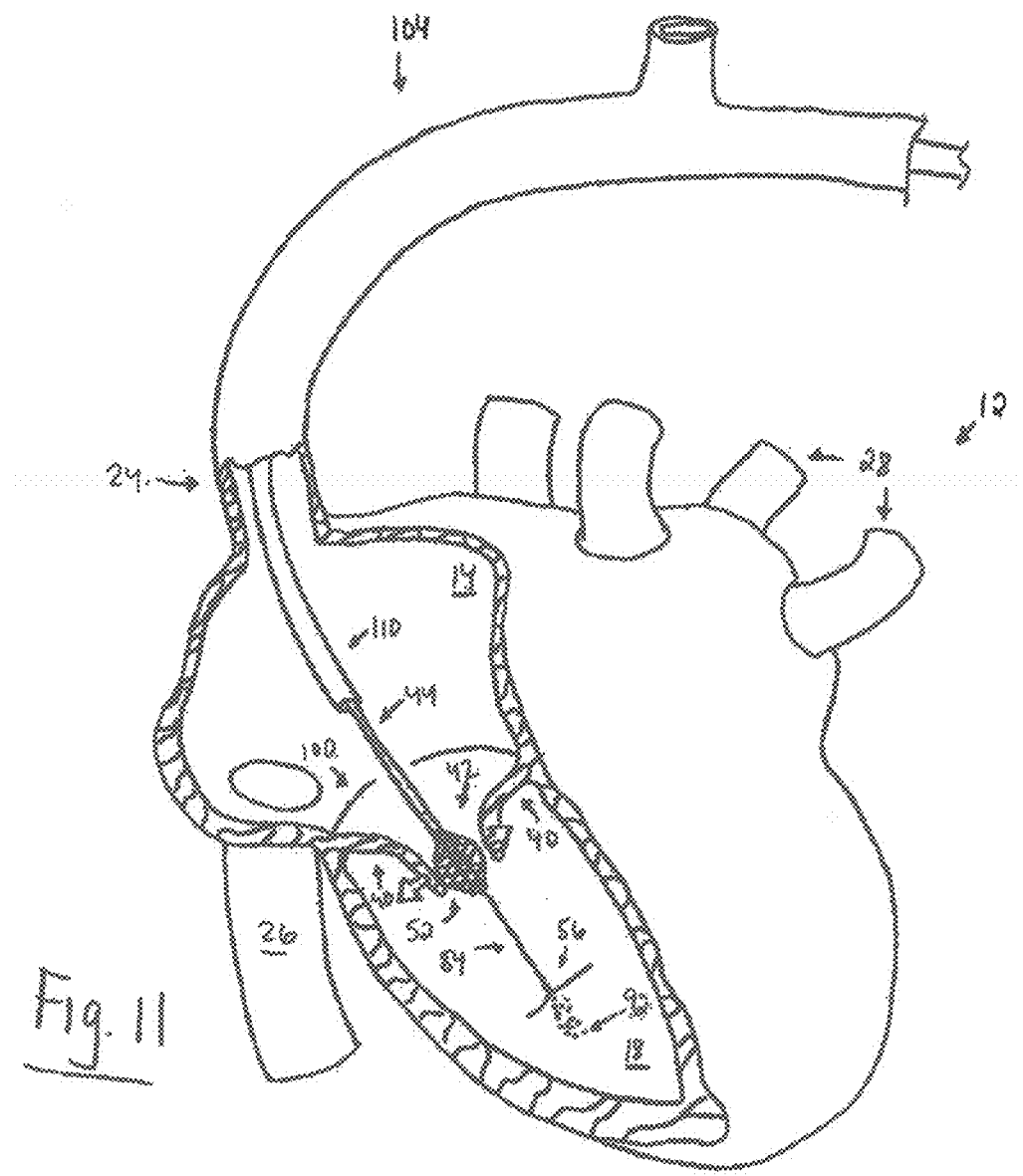
FIG. 11 is a cross-sectional view showing the diameter D of the occluding member comprising the device in FIG. 10 being increased.

After the occluding member 52 is optimally positioned in or about the diseased tricuspid valve 100, the diameter D of the occluding member can be adjusted to ensure proper coaptation of the tricuspid leaflets 40 with the outer surface 64 of the occluding member. To increase the diameter D of the occluding member 52 (indicated by arrows in FIG. 11), for example, the second handle member 96 can be rotated in a clockwise manner. Alternatively, the second handle member 96 can be rotated in a counter-clockwise manner to decrease the diameter D of the occluding member 52. Coaptation of the tricuspid valve leaflets 40 with the outer surface 64 of the occluding member 52 may be monitored by any image-based means. Where the occluding member 52 has opacity, for example, MRI or CT may be used to monitor the degree of coaptation between the tricuspid leaflets 40 and the occluding member 52. Any further adjustments to the diameter D of the occluding member 52 can then be made to ensure optimal coaptation of the tricuspid leaflets 40.

Figure 12:
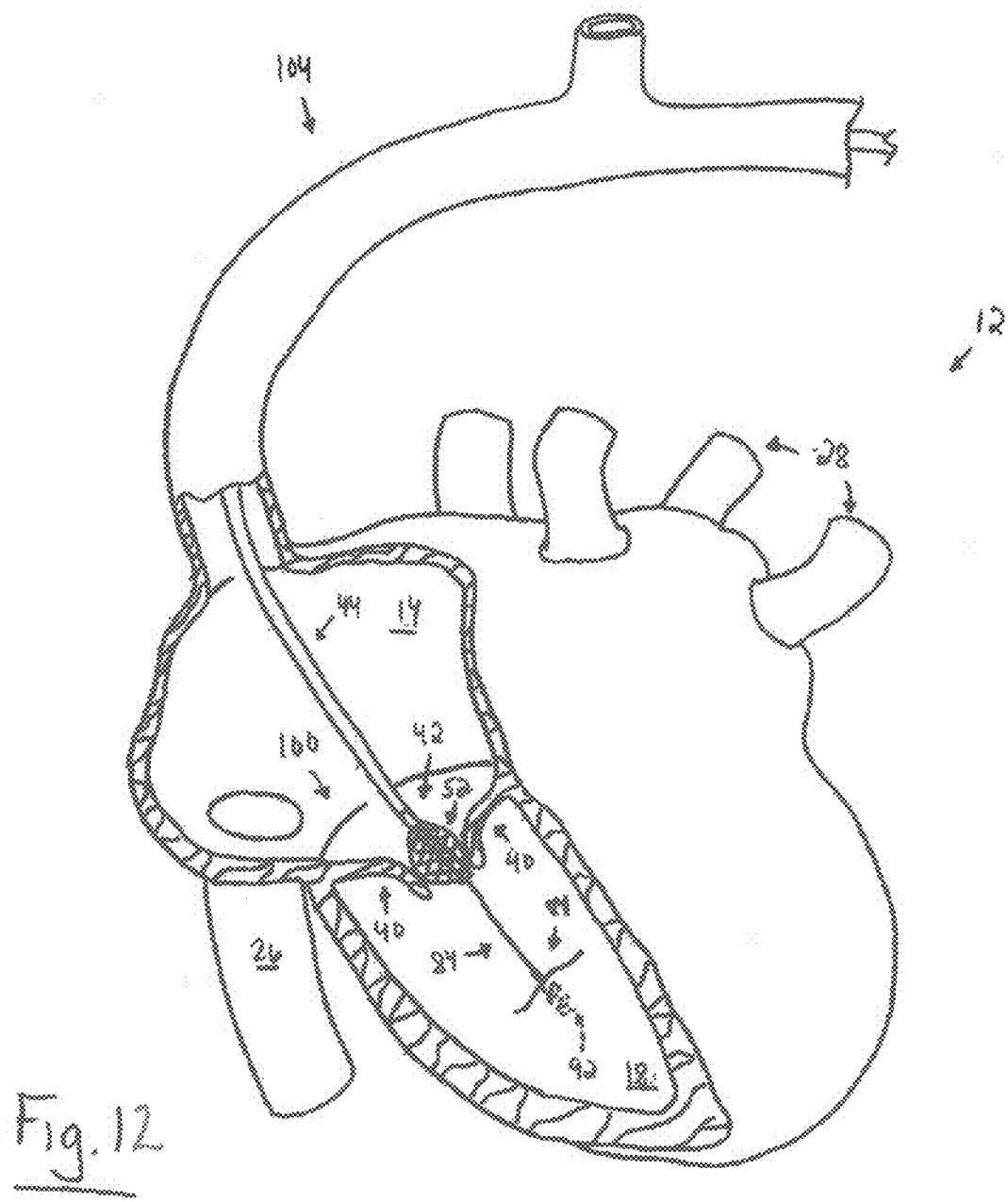
FIG. 12 is a cross-sectional view showing the device in FIG. 11 deployed in the diseased tricuspid valve.

Once the device 42 is appropriately positioned in the heart 12 of the patient (FIG. 12), the system can be at least partially or completely implanted in the subject. In one example, the adjustment member 44 can be secured within the patient in a pacemaker-like manner following implantation. Using a transvenous approach through a subclavian vein 104, for example, the proximal control end 60 of the adjustment member 44 may be sutured to muscle tissue beneath the outer skin of the patient to maintain the position of the proximal control end. A protective sheath (not shown) may be provided around the proximal control end 60. It is possible to access the proximal control end 60 of the adjustment member 44 at a later time if, for example, it is required to alter the position and/or diameter of the occluding member 52, or to remove the system 10, for example, if any part of the system becomes infected. Access may be gained by removing the protective sheath and exposing the proximal control end 60 or any other portion of the shaft that is connectable to the proximal control end.

In another example, the system 10 can be partially implanted in the subject such that only the proximal control end 60 protrudes from the subject's body. In this instance, the shape and/or position of the occluding member 52 can be adjusted, if needed, without the need to perform a surgical procedure. A physician or health care provider can simply manipulate the proximal control end 60 as need to adjust the shape and/or position of the occluding member 52 (e.g., under radiographic guidance) until optimal hemodynamics through the tricuspid valve 100 are achieved.

With the occluding member 52 appropriately positioned in the regurgitant tricuspid valve orifice, at least one leaflet 40 of the tricuspid valve 100 can coapt with the outer surface 64 of the occluding member. Consequently, the valve leaflets 40 abut the occluding member 52 and buttress the tricuspid valve 100 so that the regurgitant blood flow through the diseased tricuspid valve is substantially reduced or eliminated during systole.

It will be appreciated that a balloon-based approach may be used to first size the diseased tricuspid valve 100 prior to implantation of the system 10. Such an approach is described in U.S. Pat. No. 7,901,454 to Kapadia et al.

FIGS. 11-15 illustrate another aspect of the present invention including a method for treating regurgitation of blood through a diseased mitral valve 112. The method can be performed using the system 10 illustrated in FIG. 1. The system 10, for example, can comprise a device 42 and an adjustment member 44 that are similarly or identically constructed as the device and adjustment member described above.

Figure 13:
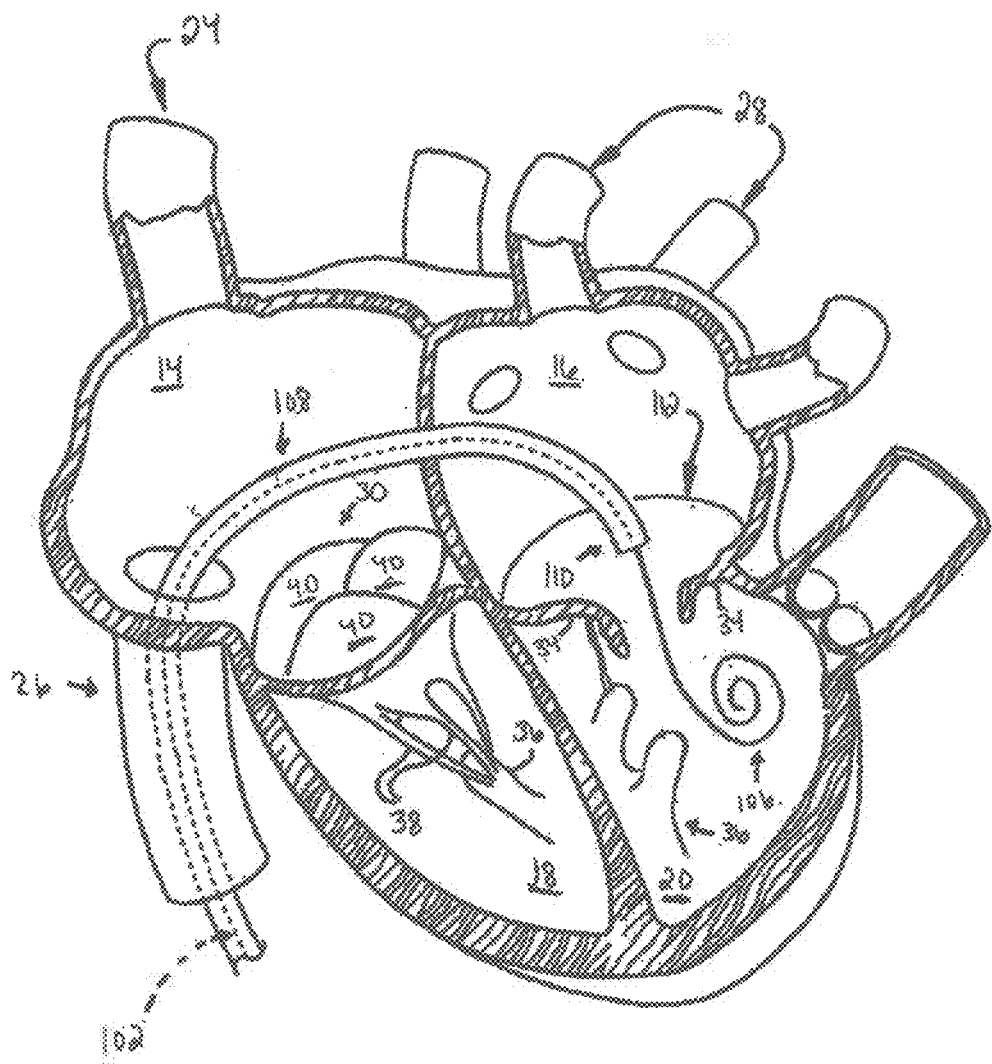
FIG. 13 is a cross-sectional view showing a catheter advanced over a guidewire into the left ventricle.

To treat regurgitation of blood through the diseased mitral valve 112, a guidewire 102 can be inserted into a patient's body via a femoral vein (not shown), jugular vein, another portion of the patient's vasculature, or directly into the body through a chest incision. Under image guidance (e.g., fluoroscopy, ultrasound, magnetic resonance, computed tomography, or combinations thereof), the guidewire 102 may be steered through the patient's vasculature into the inferior vena cava 26, for example. The guidewire 102 can then be passed across the right atrium 14 so that a distal end 106 of the guidewire pierces the interatrial septum 22 (FIG. 13). The guidewire 102 can be extended across the left atrium 16 and then downward through the diseased mitral valve 112 so that the distal end 106 of the guidewire is securely positioned in the left ventricle 20.

After the guidewire 102 is appropriately positioned in the patient's heart 12, a catheter 108 can be passed over the guidewire. The catheter 108 can then be passed over the guidewire 102 and advanced into the left atrium 16. If it has not been done so already, the system 10 can be attached to a proximal end (not shown) of the guidewire 102. An axial force is then applied to the proximal control end 60 of the adjustment member 44 so that the device 42 is passed over the guidewire 102. The device 42 can be advanced along the guidewire 102 until the device reaches a distal end portion 110 of the catheter 108.

Figure 14:
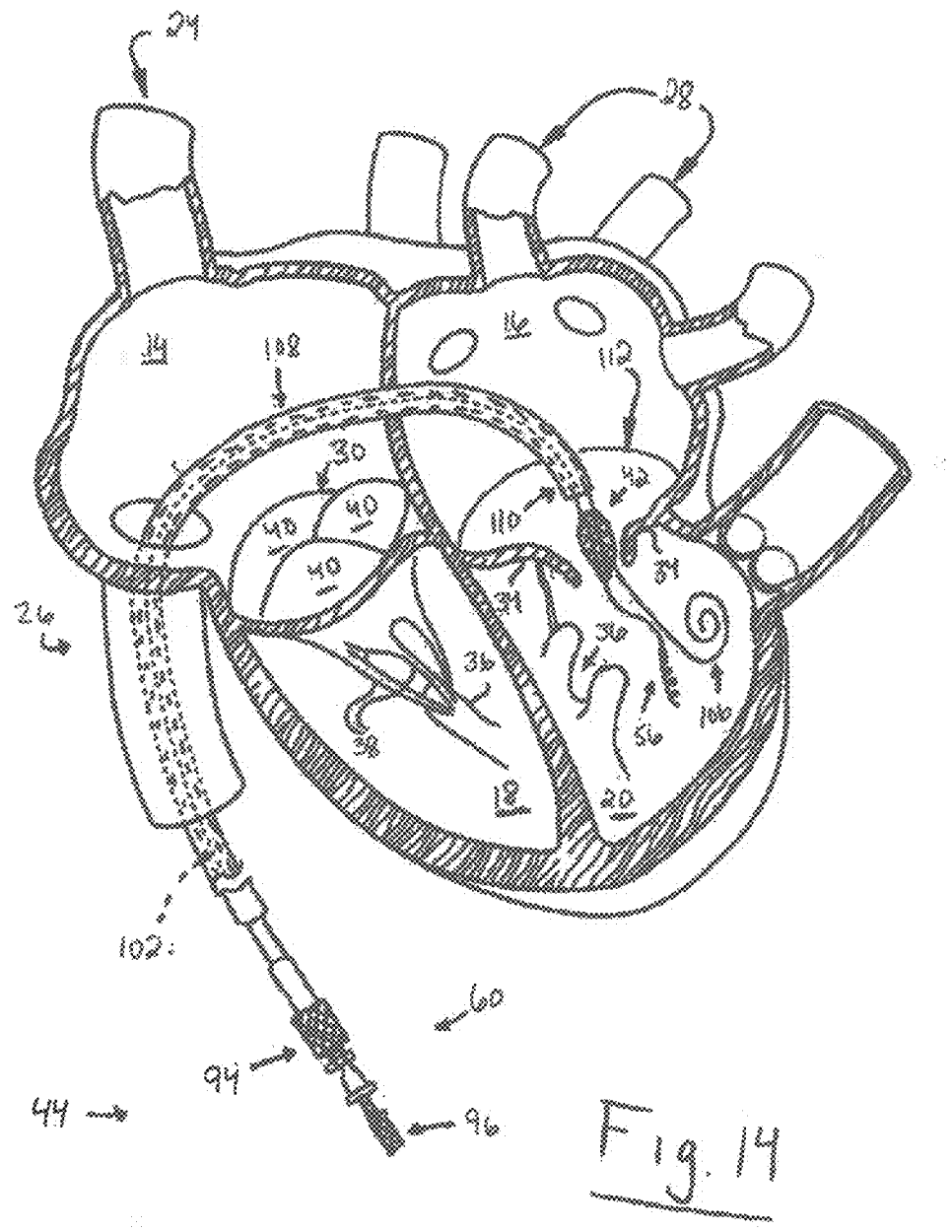
FIG. 14 is a cross-sectional view showing a device comprising the system in FIG. 1 partly deployed in a diseased mitral valve.

Upon reaching the distal end portion 110 of the catheter 108, the device 42 can be progressively freed from the catheter as shown in FIG. 14. As the device 42 is progressively freed from the catheter 108, the position of the device within the heart 12 can be monitored, controlled, and/or quality assured by imaging systems of various kinds. For example, X-ray machines, fluoroscopic machines, ultrasound, CT, MRI, PET, and other imaging devices may be used.

Figure 15:
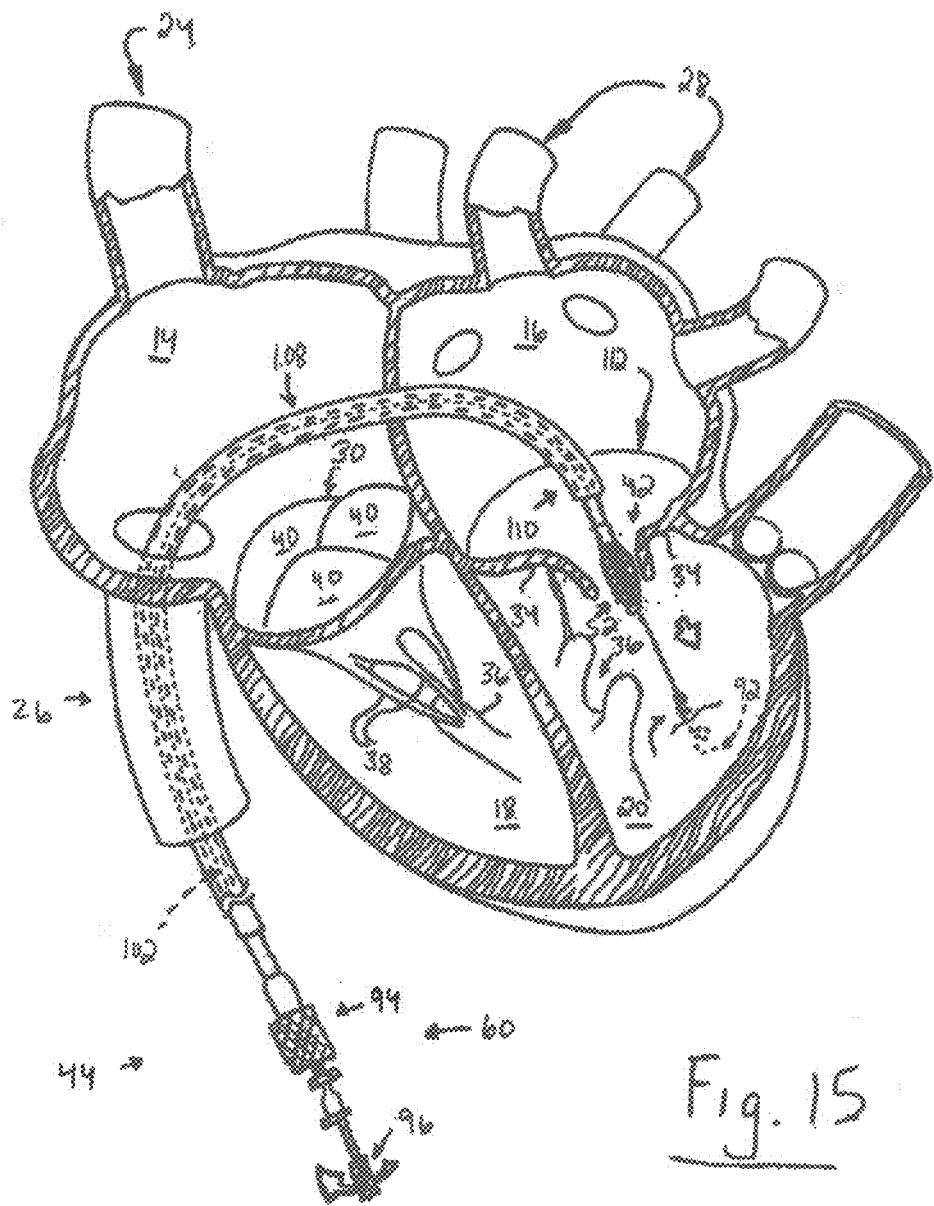
FIG. 15 is a cross-sectional view showing the device in FIG. 14 being anchored in the left ventricle.

Once the device 42 is freed from the catheter 108, the device may be appropriately positioned in the heart 12. More particularly, the anchoring member 56 may be urged toward the wall of the left ventricle 20 until the sharpened tip 92 contacts the left ventricular tissue (FIG. 15). The anchoring member 56 can be positioned within the heart 12 so that the occluding member 52 is positioned at or slightly below the level of the mitral annulus. Depending upon the location and geometry of the regurgitant mitral valve orifice, the occluding member 52 may be suspended at any one of a number of different positions. For example, the occluding member 52 may be positioned approximately level to the mitral annulus. Alternatively, the occluding member 52 may be positioned so that at least a portion of the occluding member is positioned below the free ends of the mitral valve leaflets 34.

The first handle member 94 of the proximal control end 60 can then be turned in clockwise manner, which causes the threaded wire 84 to be extruded from the collar 90 and force the sharpened tip 92 of the anchoring member 56 into the heart tissue (indicated by arrow in FIG. 15). The first handle member 94 can be operated (i.e., turned in clockwise manner) until the anchoring member 56 is substantially or entirely embedded within the heart tissue of the left ventricle 20. If needed, the position of the occluding member 52 relative to the diseased mitral valve 112 can be adjusted. To move the occluding member 52 in a superior direction, for example, the first handle member 94 can be rotated in a counter-clockwise direction, which increases the distance d of the threaded wire 84. Conversely, the occluding member 52 can be moved in an inferior direction by rotating the first handle member 94 in a clockwise direction and thereby decreasing the distance d of the threaded wire 84.

Figure 16:
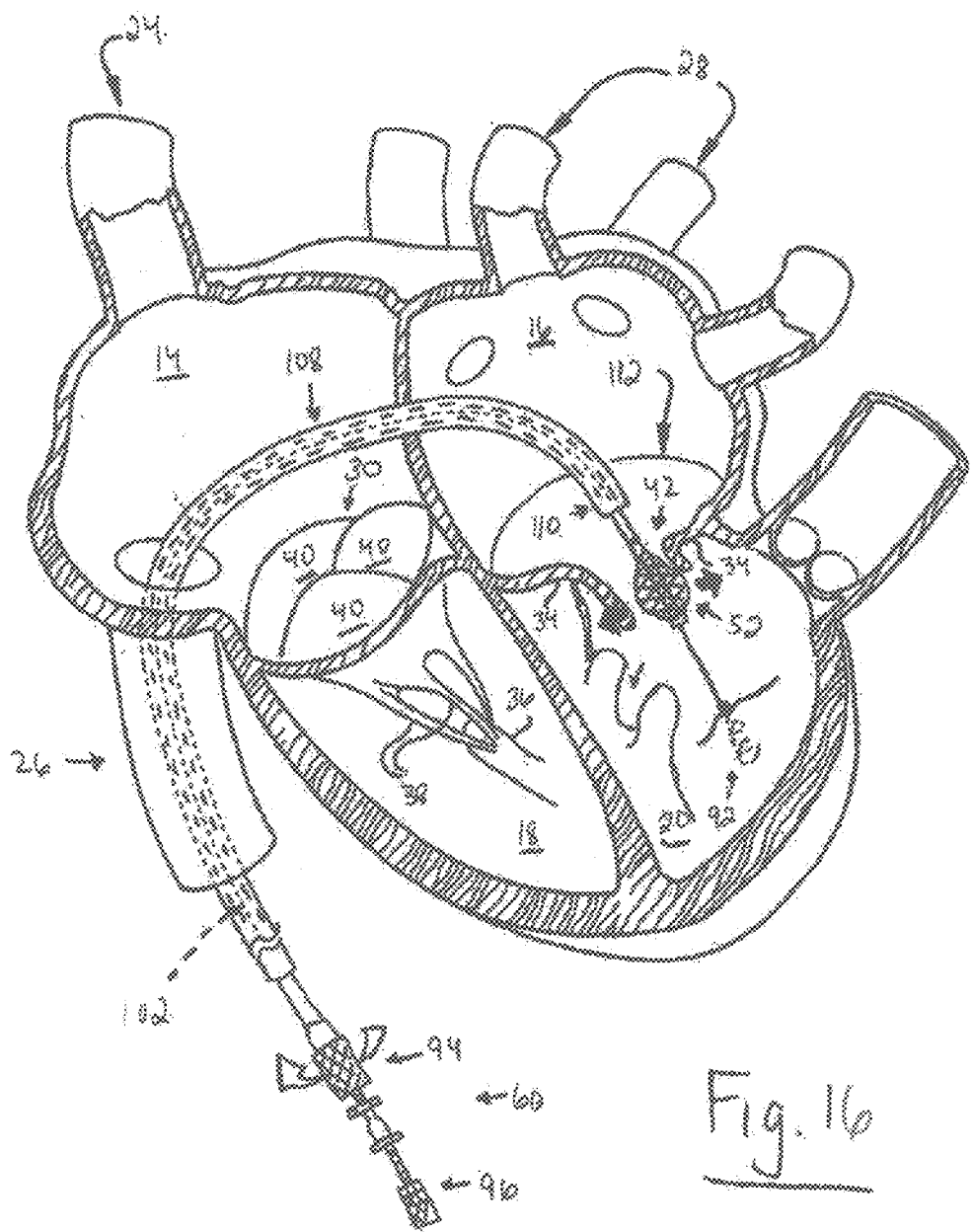
FIG. 16 is a cross-sectional view showing the diameter D of an occluding member comprising the device in FIG. 15 being increased.

After the occluding member 52 is optimally positioned relative to the diseased mitral valve 112, the diameter D of the occluding member can be adjusted to ensure proper coaptation of the mitral leaflets 34 with the outer surface 64 of the occluding member. To increase the diameter D of the occluding member 52 (indicated by arrows in FIG. 16), for example, the second handle member 96 is rotated in a clockwise manner. Alternatively, the second handle member 96 can be rotated in a counter-clockwise manner to decrease the diameter D of the occluding member 52. Coaptation of the mitral valve leaflets 34 with the outer surface 64 of the occluding member 52 may be monitored by any image-based means. Where the occluding member 52 has opacity, for example, MRI or CT may be used to monitor the degree of coaptation between the mitral leaflets 34 and the occluding member. Any further adjustments to the diameter D of the occluding member 52 can then be made to ensure optimal leaflet coaptation.

Figure 17:
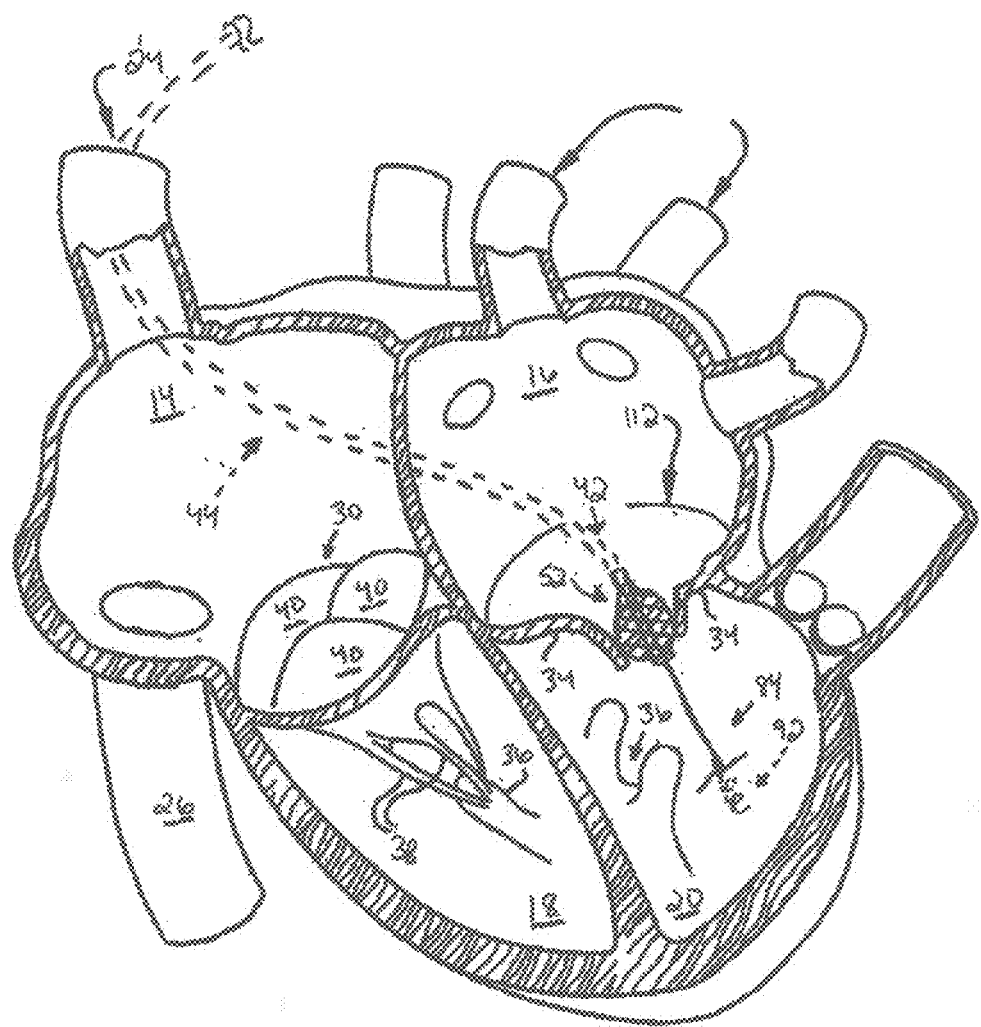
FIG. 17 is a cross-sectional view showing the device in FIG. 16 deployed in the diseased mitral valve.
Figure 18:
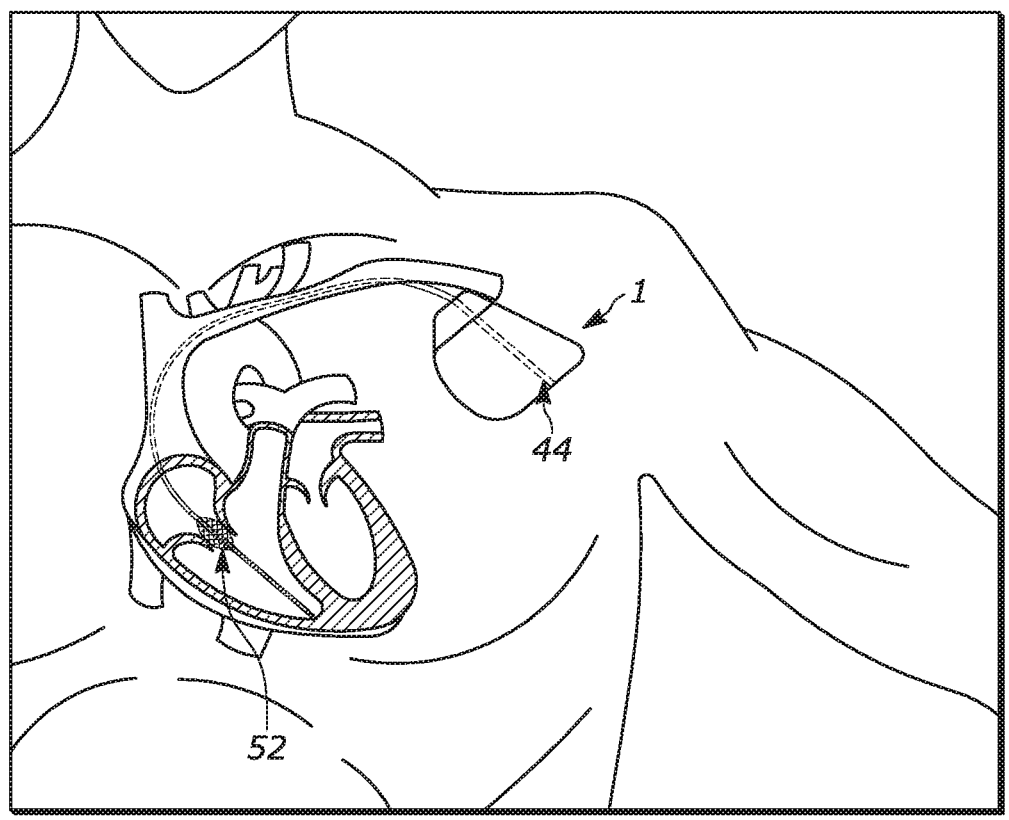
FIG. 18 is a schematic illustration showing the system, and in particular the adjustment member, of the present disclosure completely implanted in a subcutaneous pocket of a subject.
Figure 19:
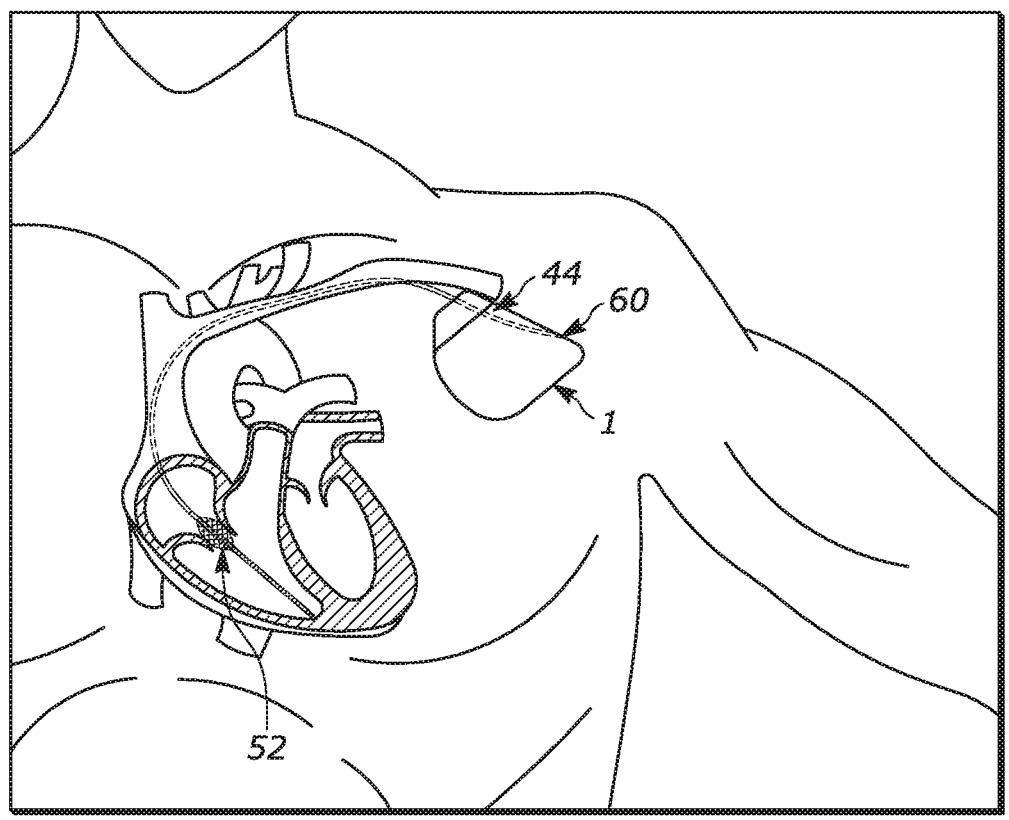
FIG. 19 is a schematic illustration showing the system, and in particular the adjustment member, of the present disclosure partially implanted in a subcutaneous pocket of a subject.

After the apparatus 42 is appropriately positioned in the heart 12 of the patient (FIG. 17), all or only a portion of the system 10 can be implanted in the subject (as described above). For example, the adjustment member 44 can be entirely implanted within a subcutaneous pocket 1 a shown in FIG. 18. Alternatively, the adjustment member 44 can be partly implanted in a subcutaneous pocket 1 (FIG. 19) so that the proximal control end 60 extends outside of the pocket (and beyond the skin of the subject. With the occluding member 52 appropriately positioned in the regurgitant mitral valve orifice, at least one leaflet 34 of the mitral valve 112 can coapt with the outer surface 64 of the occluding member. Consequently, the mitral valve leaflets 34 abut the occluding member 52 and buttress the mitral valve 112 so that the regurgitant blood flow through the diseased mitral valve is substantially reduced or eliminated during systole.

From the above description of the present disclosure, those skilled in the art will perceive improvements, changes and modifications. For example, where the system 10 is implanted from the groin toward the inferior vena cava 26 and turned toward the tricuspid valve 30, the proximal control end 60 can be completely or partially implanted within a subcutaneous pocket created in the thigh of the subject. Such improvements, changes, and modifications are within the skill of those in the art and are intended to be covered by the appended claims. All patents, patent applications, and publication cited herein are incorporated by reference in their entirety.

The following is claimed:

1. A system for treating regurgitation of blood through a diseased heart valve having at least two leaflets, the system comprising:

an implantable, lollipop-shaped device having a proximal end portion, a distal end portion, and an intermediate portion extending between the proximal and distal end portions, the intermediate portion including an expandable occluding member having a selectively adjustable diameter, at least a portion of the occluding member including a biocompatible layer attached thereto, the distal end portion including an anchoring member for securing the device in a heart chamber containing the diseased heart valve; and an adjustment member including an elongated body having a proximal control end and a distal connecting end that is operatively connected to the proximal end portion of the device;

wherein operation of the adjustment member, after implantation of the device in the diseased heart valve, causes the diameter of the occluding member to increase or decrease so that, during at least a portion of the cardiac cycle, at least one of the heart leaflet coapts with a portion of the occluding member to mitigate or prevent regurgitation of blood through the diseased heart valve;

wherein the adjustment member comprises a braided or non-braided shaft that extends from the proximal control end to the distal connecting end and is configured to exert a downward force on the device, when implanted in a subject, to ensure that the leaflets coapt with the occluding member during at least a portion of the cardiac cycle.

2. The system of claim 1, wherein the shaft further comprises one or more coils having a diameter approximately equal to a diameter of a subclavian vein such that the one or more coils exert a radial force against a wall of the subclavian vein to anchor of the device in the diseased heart valve.

3. The system of claim 1, wherein the shaft is coated with an anti-thrombogenic agent, an anti-microbial agent, or a combination thereof.

4. The system of claim 1, further comprising a release mechanism that, when actuated, separates the adjustment member from the device so that the device remains implanted in the diseased heart valve.

5. The system of claim 1, wherein the distal end portion of the device further comprises an anchor line having a distal end, the anchoring member being connected to the distal end and comprising a spiral-shaped member having a sharpened distal tip for embedding into a heart wall surrounding the diseased heart valve.

6. The system of claim 5, wherein the occluding member is configured to move axially either towards or away from the anchoring member to ensure that the leaflets coapt with the occluding member during at least a portion of the cardiac cycle.

7. The system of claim 6, wherein the anchor line includes at least one spring attached thereto to provide mechanical energy to the occluding member and ensure that the leaflets coapt with the occluding member during at least a portion of the cardiac cycle.

8. The system of claim 1, further comprising an electronic control device in electrical communication with the adjustment member, the electronic control device being configured to automatically adjust the size and/or position of the occluding member relative to the diseased heart valve based on one or more feedback parameters.

9. The system of claim 8, wherein the electronic control device is a pacemaker comprising at least one implantable lead.

10. The system of claim 1, wherein the device includes at least one sensor attached thereto for detecting one or more of intra-atrial pressure, intra-ventricular pressure, blood flow and temperature.

11. A system for treating regurgitation of blood through a diseased heart valve having at least two leaflets, the system comprising:

an implantable, lollipop-shaped device having a proximal end portion, a distal end portion, and an intermediate portion extending between the proximal and distal end portions, the intermediate portion including an expandable occluding member having a selectively adjustable diameter, at least a portion of the occluding member including a biocompatible layer attached thereto, the distal end portion including an anchoring member for securing the device in a heart chamber containing the diseased heart valve;

an adjustment member including an elongated body having a proximal control end and a distal connecting end that is operatively connected to the proximal end portion of the device; and an electronic control device in electrical communication with the adjustment member, the electronic control device being configured to automatically adjust the size and/or position of the occluding member relative to the diseased heart valve based on one or more feedback parameters;

wherein operation of the adjustment member, after implantation of the device in the diseased heart valve, causes the diameter of the occluding member to increase or decrease so that, during at least a portion of the cardiac cycle, at least one of the heart leaflet coapts with a portion of the occluding member to mitigate or prevent regurgitation of blood through the diseased heart valve.

12. The system of claim 11, wherein the electronic control device is a pacemaker comprising at least one implantable lead.

13. A system for treating regurgitation of blood through a diseased heart valve having at least two leaflets, the system comprising:

an implantable, lollipop-shaped device having a proximal end portion, a distal end portion, and an intermediate portion extending between the proximal and distal end portions, the intermediate portion including an expandable occluding member having a selectively adjustable diameter, at least a portion of the occluding member including a biocompatible layer attached thereto, the distal end portion including an anchoring member for securing the device in a heart chamber containing the diseased heart valve;

an adjustment member including an elongated body having a proximal control end and a distal connecting end that is operatively connected to the proximal end portion of the device; and at least one sensor attached thereto for detecting one or more of intra-atrial pressure, intra-ventricular pressure, blood flow and temperature;

wherein operation of the adjustment member, after implantation of the device in the diseased heart valve, causes the diameter of the occluding member to increase or decrease so that, during at least a portion of the cardiac cycle, at least one of the heart leaflet coapts with a portion of the occluding member to mitigate or prevent regurgitation of blood through the diseased heart valve.

* * * * *